(12) United States Patent
Tiefenthaler

(10) Patent No.: US 9,341,573 B2
(45) Date of Patent: May 17, 2016

(54) WAVEGUIDE GRATING STRUCTURE AND OPTICAL MEASUREMENT ARRANGEMENT

(71) Applicant: Artificial Sensing Instruments ASI AG, Zurich (CH)

(72) Inventor: Kurt Tiefenthaler, Zurich (CH)

(73) Assignee: ARTIFICIAL SENSING INSTRUMENTS ASI AG, Zurich (CH)

(*) Notice: Subject to any disclaimer, the term of this patent is extended or adjusted under 35 U.S.C. 154(b) by 0 days.

(21) Appl. No.: 14/919,202

(22) Filed: Oct. 21, 2015

(65) Prior Publication Data

US 2016/0041096 A1    Feb. 11, 2016

Related U.S. Application Data

(60) Continuation of application No. 13/932,278, filed on Jul. 1, 2013, now Pat. No. 9,170,201, which is a continuation of application No. 12/576,740, filed on Oct. 9, 2009, now Pat. No. 8,503,833, which is a continuation of application No. 10/885,449, filed on Jul. 6, 2004, now Pat. No. 7,627,201, which is a division of application No. 10/344,142, filed as application No. PCT/CH01/00486 on Aug. 9, 2001, now Pat. No. 6,785,433.

(30) Foreign Application Priority Data

Aug. 9, 2000  (CH) .................. 1559/00

(51) Int. Cl.
| | |
|---|---|
| G02B 6/00 | (2006.01) |
| G01N 21/64 | (2006.01) |
| G02B 6/124 | (2006.01) |
| G02B 6/32 | (2006.01) |

(52) U.S. Cl.
CPC .............. *G01N 21/648* (2013.01); *G02B 6/124* (2013.01); *G02B 6/32* (2013.01); *G01N 2021/6463* (2013.01); *G01N 2201/08* (2013.01)

(58) Field of Classification Search
None
See application file for complete search history.

(56) References Cited

U.S. PATENT DOCUMENTS

| | | |
|---|---|---|
| 3,856,404 A | 12/1974 | Hershier |
| 4,299,486 A | 11/1981 | Nogami et al. |
| 4,344,438 A | 8/1982 | Schultz |

(Continued)

FOREIGN PATENT DOCUMENTS

| | | |
|---|---|---|
| DE | 19615366 | 10/1997 |
| EP | 0455067 | 11/1991 |

(Continued)

OTHER PUBLICATIONS

R. Magnusson and S.S. Wang et al; New principle for optical filters; Appl. Phys. Lett. 61 (9) 31 Aug. 1992; pp. 1022-1024.

(Continued)

*Primary Examiner* — Ryan Lepisto
*Assistant Examiner* — Erin Chiem
(74) *Attorney, Agent, or Firm* — Rankin, Hill & Clark LLP

(57) ABSTRACT

The present invention describes (bio)chemo-functional waveguide grating structures consisting of at least one (bio) chemo-functional waveguide grating structure unit or at least one (bio)chemo-functional sensor location with beam guidance permitting light beam separation, as well as detection methods for parallel analysis which are marking-free or based on marking.

18 Claims, 11 Drawing Sheets

(56) References Cited

U.S. PATENT DOCUMENTS

| | | | |
|---|---|---|---|
| 4,815,843 | A | 3/1989 | Tiefenthaler et al. |
| RE33,064 | E | 9/1989 | Carter et al. |
| 4,952,056 | A | 8/1990 | Tiefenthaler |
| 5,071,248 | A | 12/1991 | Tiefenthaler et al. |
| 5,369,722 | A | 11/1994 | Heming et al. |
| 5,372,135 | A | 12/1994 | Mendelson et al. |
| 5,480,687 | A | 1/1996 | Heming et al. |
| 5,577,137 | A | 11/1996 | Groger et al. |
| 5,623,561 | A | 4/1997 | Hartman |
| 5,675,691 | A | 10/1997 | Edlinger et al. |
| 5,738,825 | A | 4/1998 | Rudigier et al. |
| 5,759,494 | A | 6/1998 | Szlosek |
| 5,822,472 | A | 10/1998 | Danielzik et al. |
| 5,831,736 | A | 11/1998 | Lichtman et al. |
| 5,835,223 | A | 11/1998 | Zwemer et al. |
| 6,078,705 | A | 6/2000 | Neuschafer et al. |
| 6,395,558 | B1 | 5/2002 | Duveneck et al. |
| 6,455,004 | B1 | 9/2002 | Tiefenthaler |
| 6,483,096 | B1 | 11/2002 | Kunz et al. |
| 6,600,563 | B1 | 7/2003 | Bahatt et al. |
| 6,610,351 | B2 | 8/2003 | Shchegolikhin et al. |
| 6,648,640 | B2 | 11/2003 | Rubbert et al. |
| 6,694,067 | B1 | 2/2004 | O'Keefe |
| 6,787,110 | B2 | 9/2004 | Tiefenthaler |
| 6,873,764 | B2 | 3/2005 | Maisenholder et al. |
| 6,958,131 | B2 | 10/2005 | Tiefenthaler |
| 2002/0025490 | A1 | 2/2002 | Shchegolikhin |
| 2003/0096210 | A1 | 5/2003 | Rubbert et al. |
| 2003/0168587 | A1 | 9/2003 | Tiefenthaler |

FOREIGN PATENT DOCUMENTS

| | | |
|---|---|---|
| EP | 0 482 377 | 4/1992 |
| EP | 0533074 | 3/1993 |
| EP | 0617273 | 9/1994 |
| JP | 59168309 | 9/1984 |
| WO | 81/00912 | 4/1981 |
| WO | 91/10122 | 7/1991 |
| WO | 92/19976 | 11/1992 |
| WO | 99/13320 | 3/1993 |
| WO | 95/03538 | 2/1995 |
| WO | 95/33198 | 12/1995 |
| WO | 96/35940 | 11/1996 |
| WO | 01/13096 | 2/2001 |

OTHER PUBLICATIONS

Ranald M. Sutherland et al.; Immunoassays at a Quartz-Liquid Interface: Theory, Instrumentation and Preliminary Application to the Fluorescent Immunoassay of Human Immunoglobulin G; Journal of Immunological Methods, 74 (1984); pp. 253-265.

S.S. Wang and R. Magnusson; Design of waveguide-grating filters with symmetrical line shapes and low sidebands, Optical Society of America, Optics Letters, Jun. 15, 1994, vol. 19, No. 12; pp. 919-921.

A. Sharon et al.; Resonant grating-waveguide structures for visible and near-infrared radiation; Journal of the Optical Society of America, vol. 14, No. 11, Nov. 1997/J. Opt. Soc. Am. A; pp. 2985-2993.

A. Sharon et al.; Light modulation with resonant grating-waveguide structures; Optical Society of America, Optics Letters, vol. 21, No. 19, Oct. 1, 1996; pp. 1564-1566.

W.A. Challenger et al.; A multilayer grating-based evanescent wave sensing technique; Sensors and Actuators B 71 (2000); Elsevier Science V.V.; pp. 42-46.

K. Tiefenthaler and W. Lukosz: Embossing Technique for Fabricating IO Components in Hard Inorganic Waveguiding Materials; 2nd European Conference on Integrated Optics, Florence, Oct. 1983, IEEE (Inst. Electr. Eng., London), conf. Publication No. 227; pp. 108-111.

W. Lukosz and K. Tiefenthaler; Directional Switching in Planar Waveguides Effected by Adsorption-Desorption Processes; 2nd European Conference on Integrated Optics, Florence, Oct. 1983, IEEE (Inst. Electr. Eng., London), conf. Publication No. 227; pp. 152-155.

W. Lukosz and K. Tiefenthaler; Embossing technique for fabricating integrated optical components in hard inorganic waveguiding materials; Optical Society of America, Optics Letters, vol. 8, Oct. 1983; pp. 537-539.

K. Tiefenthaler and W. Lukosz; Integrated optical switches and gas sensors; Optical Society of America, Optics Letters, vol. 9, Apr. 1984; pp. 137-139.

K. Tiefenthaler and W. Lukosz; Grating Couplers as Integrated Optical Humidity and Gas Sensors; Electronics and Optics; Thin Solid Films, 126 (1985); pp. 205-211.

M. Seifert et al.; An Integrated Optical Biosensor (IOBS); Analytical Letters, 19 (1&2), (1986); pp. 205-216.

K. Tiefenthaler and W. Lukosz; Sensitivity of grating couplers as integrated-optical chemical sensors; Journal fo the Optical Society of America; vol. 6, No. 2, Feb. 1989, J. Opt. Soc.Am. B; pp. 209-219.

M. Nellen et al; Integrated Optical Input Grating Couplers as Biochemical Sensors; Sensors and Actuators, 15 (1988); Elseveier Sequoia; pp. 285-295.

W. Lukosz and K. Tiefenthaler; Sensitivity of Integration Optical Grating and Prism Couplers as (Bio)Chemical Sensors; Sensors and Actuators, 15 (1988); Elsevier Sequoia; pp. 273-284.

J. Dubendorfer, et al.; Reference pads for miniature integrated optical sensors, Paul Scherrer Institute, Zurich Switzerland, Sensors and Actuators B 38-39 (1997) 116-121.

Tom O'Brien, et al.; The development of immunoassays to four biological threat agents in a bidiffractive grating biosensor, Biosensors & Bioelectronics 14 (2000) 815-828.

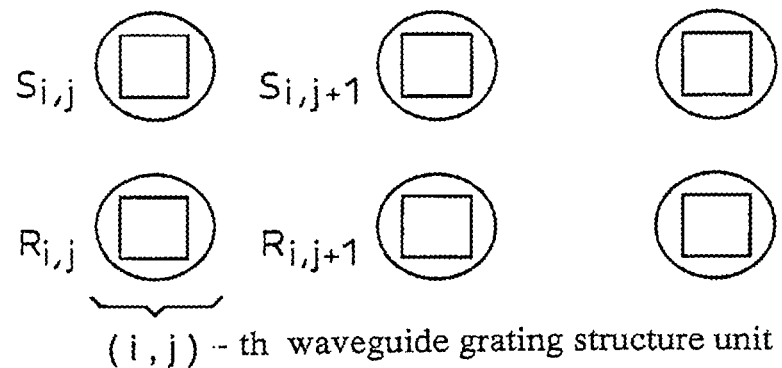
(i,j) -- th waveguide grating structure unit
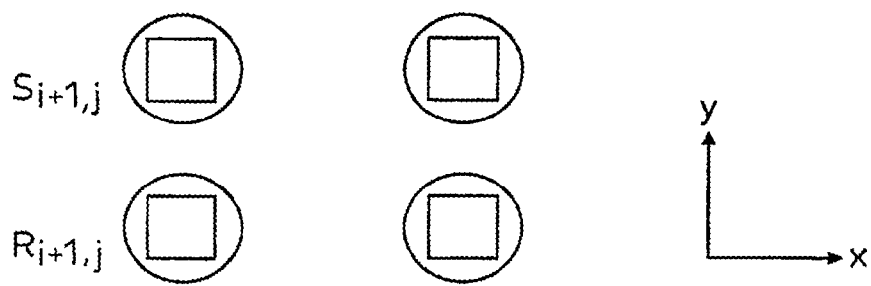
FIG. 7
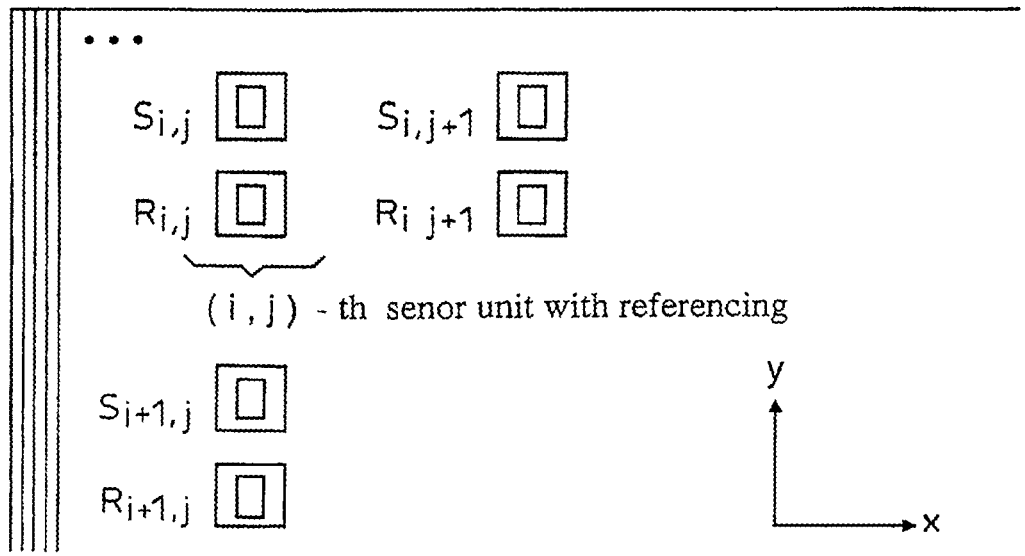
(i,j) -- th senor unit with referencing
FIG. 8

WAVEGUIDE GRATING STRUCTURE AND OPTICAL MEASUREMENT ARRANGEMENT

BACKGROUND OF THE INVENTION

Various waveguide grating structures have already been described in the PCT applications PCT/EP94/02361 and PCT/CH98/00389. The beam guiding, however, is not optimal. The reflected beam of a first incident light wave coincides with the direction of a second incident light wave. The reflected light beam and the second incident light beam oppositely have the same direction, which may lead to perturbations. The PCT applications PCT/EP94/02361 and PCT/CH98/00389 do not illustrate how a waveguide grating sensor structure that consists of two-dimensionally arranged sensor locations may be read out in parallel in the case of detection free of marking. Parallel reading-out is, however, necessary in order to achieve a higher throughput.

In the European patent application EP 0 482 377 A2 the waveguide grating is illuminated with a focussing light field. A focussing light field is not suitable for simultaneous illumination of a two-dimensional array of waveguide grating sensors. Furthermore, there is no mention of a method for temperature compensation in this application.

In Sensors and Actuators B 38-39 (1997), 116-121, a sensor location and a reference location of the waveguide grating are illuminated using the multiplex method. Also there is shown no one-dimensional or two-dimensional beam expansion of the incident light beam.

SUMMARY OF THE INVENTION

The present invention achieves the object of creating an optical sensor which:
(1) simultaneously illuminates several one-dimensionally or two-dimensionally arranged sensor locations based on waveguide grating structures via suitable beam expansion optics;
(2) ensures the separation of light fields or light beams;
(3) produces light fields on a detector or detector array (e.g. pixel array detector), which do not superimpose on the detector or detector array;
(4) generates measurement signals on non-reflected light fields;
(5) generates measurement signals that have a low temperature dependence;
(6) carries out measurements in a scanning mode method without moving mechanics and with a large dynamic range;
(7) for determining the resonance location, evaluates the scan distribution (i.e. the light intensity measured in a certain detector range as a function of the scan parameter, and/or the light intensity measured in a certain detector range as a function of the detector coordinates) with a center of intensity method or with a data fit of a part of the scan distribution (region of the maximum, region of the maximal rise (gradient), region of the constant rise (gradient));
(8) generates referenced sensor signals by way of evaluating a signal path and at least one reference path;
(9) increases the measurement accuracy by way of scan averaging methods or resonance location averaging methods; and,
(10) permits the evaluation of micro-plates, micro-arrays and lab-on-chips.

The invention also suggests waveguide grating structure units that permit a separation of the incident, reflected, or diffracted light beams without the beam path having to be tilted with respect to the plane of incidence. Furthermore, the reading out of the four out-coupled modes TE+, TE−, TM+, TM− (notation: TE+: transverse electric mode in (+x) direction (forward direction), TE−: transverse electric mode in the rearward direction, TM+: transverse magnetic mode in the forward direction, TM−: transverse magnetic mode in the rearward direction) may be effected on a single one-dimensional or two-dimensional position-sensitive detector (e.g. pixel array detector), wherein preferably between the detector and the waveguide grating structure there are arranged lens optics. If one-dimensional or two-dimensional arrays of waveguide grating structure units (for example arrays of sensor locations) are used, as they are for example applied with micro-plates or micro-arrays, it is recommended to operate with a two-dimensional pixel array detector, since all out-coupled and/or radiated light waves may be incident on the two-dimensional detection surface. The arrays of waveguide grating structure units (for example arrays of sensor locations) may be arranged on a round or polygonal (rectangular) disc (plate) in a Cartesian, matrix-like, or circular-(ring)-shaped manner.

BRIEF DESCRIPTION OF THE DRAWINGS

These and further features of the invention will be apparent with reference to the following description and drawings, wherein:

FIGS. 6 and 7 show an array of waveguide grating structure units (i,j) consisting of a signal path S(i,j) and a reference path R(i,j);

FIG. 8 shows an array of sensor units (i,j) consisting of a signal path S(i,j) and a reference path R(i,j) on a large waveguide grating;

DETAILED DESCRIPTION OF THE PREFERRED EMBODIMENTS

Figure 1:
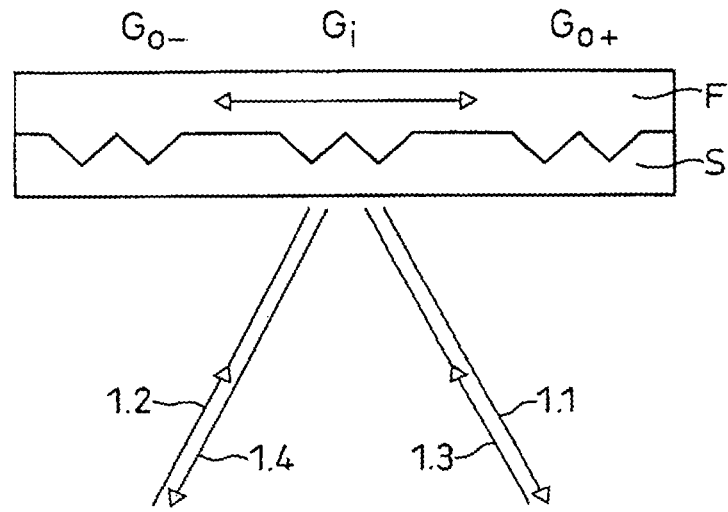
FIG. 1 shows a three-grating arrangement with a coincident beam guiding.

FIG. 1 shows a three-grating arrangement with a coincident beam guiding. The reflected beam 1.1 of the left incident light wave 1.2 runs directly opposite the right incident light wave 1.3 (with reflection beam 1.4). The middle grating is the in-coupling grating $G_I$. Located to the left and right of this are the two out-coupling gratings $G_{0+}$ and $G_{0-}$. The wave-guiding film F is located on the substrate S. The arrows in the wave-guiding film F represent the propagation direction of the modes. With a perpendicular incidence of light the reflected light beam indeed runs back in itself. If the light source is specially a laser source (laser diode source), then a coincident guiding of the beam may cause laser fluctuations since an external resonator is connected to the actual laser resonator. Laser fluctuations create instabilities in the measurement signal.

Figure 2A:
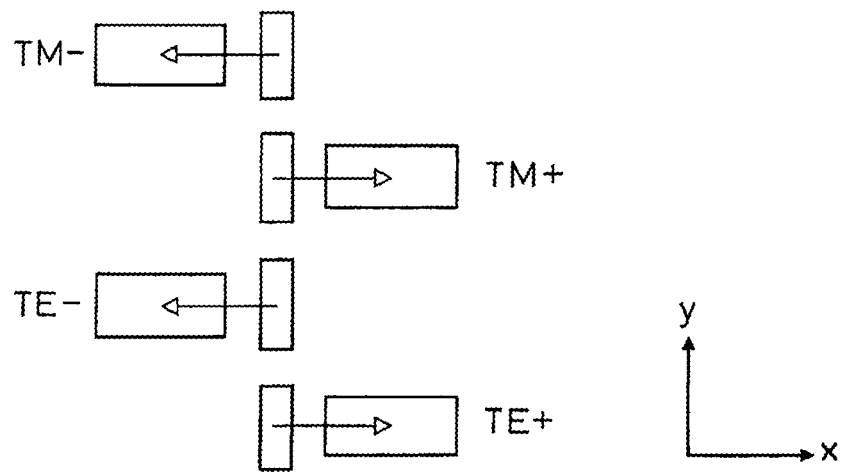
FIGS. 2a, 2b, and 2c show waveguide grating structure units that may also be arranged in an array-like manner.
Figure 2B:
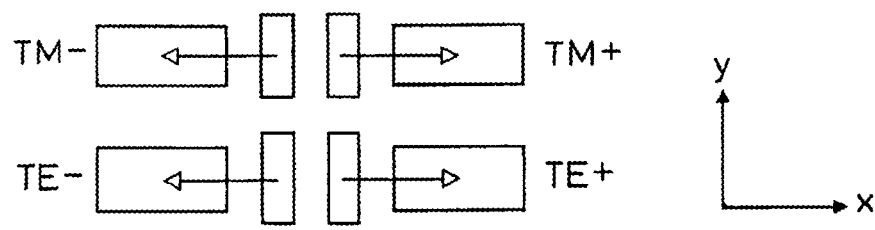
Figure 2C:
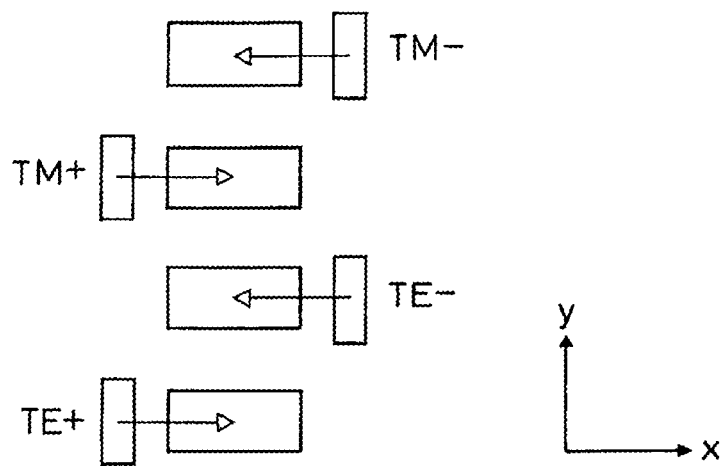
Figure 3A:
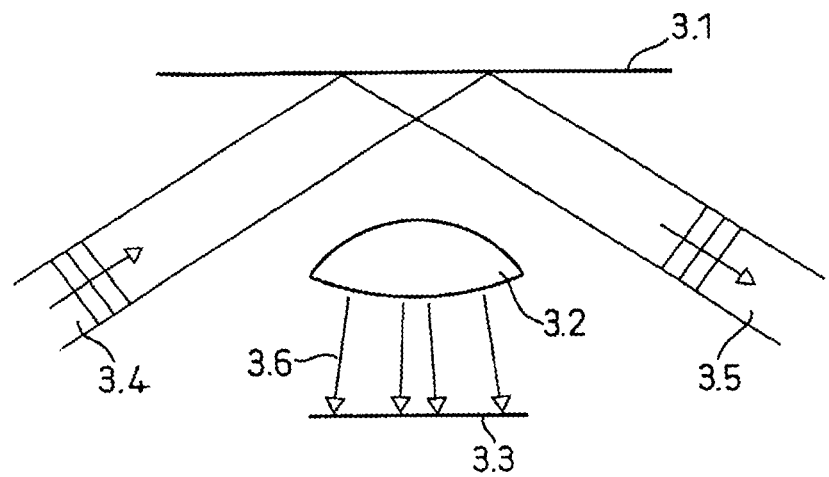
FIGS. 3a, 3b, 4a, 4b, 5a, 5b show various measurement arrangements.

FIGS. 2a, 2b, and 2c show special waveguide grating structure units of a waveguide grating structure, wherein the small rectangles represent the in-coupling gratings and the large rectangles the out-coupling gratings. The grating lines are parallel to the y-axis. The grating periods in each case are selected such that mode excitation and mode out-coupling is possible with the suggested measuring arrangements (see FIGS. 3, 4 and 5). In FIGS. 2a to 2c a stop grating (or a stop taper or a stop slot) may further be located after the out-coupling grating. The stop grating diffracts the remaining mode light in a direction that is not relevant to the measurement. FIG. 2c represents a compact form of a waveguide grating structure unit since the extension of the waveguide grating structure unit in the x-direction is smaller than in FIGS. 2a and 2b. There, of course, also exist symmetrical variants of FIGS. 2a, 2b, and 2c. For example, the figures may be rotated by 180 degrees. The in-coupling gratings may be more heavily modulated than the out-coupling grating. The modes to be excited TE+, TE−, TM+, TM− preferably with a mode number m=0 are drawn in and indicated as arrows. The sequence of the four sensing pads, which in each case consist of an in-coupling grating and an out-coupling grating, as also the sequence of the modes to be excited, may be exchanged without limiting the universality. The sensing pads may be designed as planar waveguides or as strip waveguides.

In FIGS. 2a, 2b, and 2c, a waveguide grating structure unit in each case consists of four sensing pads. Each sensing pad is allocated to one of the four modes. However, also in each case two sensing pads (where appropriate also all four sensing pads) may be superimposed. By way of this bi-diffractive or multi-diffractive gratings are applied. The superimposition of two sensing pads is described by way of FIG. 2. The sensing pad responsible for the mode TE− is superimposed on the sensing pad responsible for the mode TM−. The sensing pad responsible for the mode TE+ is superimposed on the sensing pad responsible for the mode TM+. In the FIG. 2 there may be present only one sensing pad for a mode X=TE+(TM+) in the (+x)-direction and one sensing pad for a mode X=TE−(TM−) in the (−x)-direction.

The waveguide structure may consist of (an array of) strip waveguides and/or of a wave-guiding film (of e.g. $TiO_2$, $Ta_2O_5$, $ZrO_2$, $Si_3N_4$, etc.) and/or of a layer system of several layers, wherein it must be ensured that the layer system has wave-guiding properties. Thus, the effective refractive index N of the guided light wave (with mode number m=0, 1, 2 . . . ) must be larger than the refractive index of the substrate and larger than the refractive index of the cover medium. Preferably, a layer with a high refractive index is present in the layer system. The high refractive index ensures a high electromagnetic field strength on the surface of the waveguide and, thus, a high sensitivity on detection of surface phenomena (adsorption, selective binding occurrences, surface reactions, holistic cell occurrences, etc.). Absorbing waveguide structures may also be applied. The substrate may consist of a transparent material (glass or plastic).

The manufacture of waveguide structures and the materials, which are applied with this, are described in the PCT applications PCT/EP94/02361 and PCT/CH98/00389. The waveguide grating structure arrangements described in the PCT applications PCT/EP94/02361 and PCT/CH98/00389 may likewise be supplemented with stop gratings, stop tapers, or stop slots. All waveguide grating structures—also those of PCT/EP94/02361 and PCT/CH98/00389—may be illuminated with one light wave whose wave vector component parallel to the grating lines is slightly different than zero.

The gratings may be rectangular gratings, sinusoidal (cosinusoidal) gratings, saw-tooth gratings, etc. The gratings may be dry-etched or wet-etched or be manufactured by a replication method ((hot-)embossing technology, injection molding methods (with or without compression step(s), etc). The masks may be manufactured photo-lithographically, where appropriate with the application of an electron beam. One requires masks for the manufacture of the gratings or the mold pattern, respectively. The grating may be located on an interface of the waveguide structure (i.e. at the interface of a layer of the waveguide structure) or in the waveguide structure. The gratings may also be focussing.

A waveguide grating structure unit becomes chemo-sensitive (chemo-functional) in that a chemo-sensitive substance at least in the region of the sensor grating (at least partly) is deposited onto (or introduced into) the waveguide grating structure unit. In the out-coupling angle scanning mode (see further below) the out-coupling gratings correspond to the sensor gratings, in the incident angle scanning mode (see further below) or in the wavelength scanning mode (see further below) the in-coupling gratings correspond to the sensor gratings. If bio(molecules) bind to the (bio)chemo-sensitive substance, then the (possibly complex) effective refractive index of a guided light wave changes.

Since the sensor grating on the waveguide grating structure unit is sometimes locally limited, it is advantageous if the chemo-functional layer covers the complete sensor grating. The edge of the chemo-functional layer runs outside the sensor grating. It is also advantageous if the complete sensor grating (with a plane wave and/or a guided wave) and the local vicinity surrounding the sensor grating is illuminated. A small beam stirring thus has no effect (at least in the case where one operates with a signal path and a reference path), since then even with beam stirring the complete sensor grating is still illuminated.

Apart from (bio)molecular binding partners (such as e.g. antibodies, antigens, receptors, peptides, phages, single stranded DNA(RNA) sections, genes, gene sections, targets, proteins, binding proteins, enzymes, inhibitors, nucleic acids, nucleotides, oligonucleotides, SNP, allergens, pathogens, carbohydrates, metabolites, hormones, etc.) one may also apply molecular imprinted polymers (such as, for example, plastic antibodies, plastic antigens, etc.) or (living) cells as (bio)chemo-functional layers. The bonding procedures (or the (bio)chemical reactions) here too may be effected at the surface, in the volume, or at the surface as well as in the volume of the (bio)chemo-functional layer.

A waveguide grating structure unit may also be applied for referencing. The sensor signal S of the signal waveguide grating structure unit may be referenced with the sensor signal R of the reference waveguide grating structure unit. The chemo-functional signal layer (at least partly) covers the signal waveguide grating structure unit (signal path), and the chemo-functional reference layer (at least partly) covers the reference waveguide grating structure unit (reference path). The referenced sensor signal $S_{ref}$ is then $S_{ref}=S-R$. The edging of the chemo-functional layers may also lie outside the gratings. A chemo-functional layer may also at least partly cover the complete waveguide grating structure unit.

One may envisage a waveguide grating structure unit especially for the referencing also as follows: With two (neighbouring) waveguide grating structure units in each case there is present only one sensing pad. The other sensing pads are brought to disappear via modulation intensity=0, thus are not present. The thus generated waveguide grating structure units are, however, to be considered as belonging to the FIGS. 2a, 2b, and 2c in that the modulation intensity (=0) is perceived to be a grating characteristic. The two (lying next to one another at any distance) sensing pads (in each case with one in-coupling grating an one out-coupling grating or, where appropriate, with only one in-coupling grating) of the two waveguide grating structure units with preferably the same mode carry different chemo-functional layers as is described in the patent application WO 99/13320. By referencing the two measurement signals (sensor signal and reference signal), for example, by subtraction of the two out-coupling angles in the out-coupling angle scanning mode or by subtracting the two resonance wavelengths for grating in-coupling in the wavelength scanning mode (see further below) or by subtracting the two resonance incident angles for grating in-coupling in the incident angle scanning mode (see further below) the drift present on both sensing pads (such as temperature drift, thermo-optical drift, photo-chemical drift, wavelength drift, incident angle drift etc.) may be eliminated. The wavelength-dependent sensitivity may be also taken into account when referencing. With referencing with modes of different polarization and/or mode number, the different sensitivity of the polarization and/or mode number must be taken into account.

The chemo-functional reference layer should have the same or almost the same non-specific binding (NSB) as the chemo-sensitive signal layer or no or almost no NSB. The chemo-functional reference layer may indeed also contain specific binding partners as long as one, on account of previous information, knows that no analyte of the sample may bind to these binding partners. With comparative studies one may also envisage that the (or an) analyte of the sample indeed binds to the specific binding partners of the chemo-functional reference layer.

The chemo-functional layers may also be (living) cells (human, animal, plant cells, etc.) where appropriate on modified surfaces (silane layers, polymer layers, lipid layers (with or without ion channels, monolayers, bilayers, etc.) or biocompatible surfaces. The reference path contains—if present—other (or modified) cells. The (liquid) sample for the signal and reference path may be equal or different. In place of biomolecular interactions here the cell behaviour is studied holistically (as a whole) by measurement of (complex) effective changes in the refractive index (and variables deduced from this) on cells, or changes of fluorescence (luminescence) signals on cells (marked with fluorescence or luminescence). The cell coverage density of the two paths should be equal or almost equal (perhaps up to the signal-to-noise ratio of the referenced measurement signal).

In a waveguide grating structure unit the sensing pads for the one mode (in the forward and rearward direction) (e.g. TE+, TE−) may also be seen as a reference path for the sensing pads with the other mode (in the forward and rearward direction) (e.g., TM+, TM−) (=signal path) (or also vice-versa). If a chemo-functional layer covers both paths, then the chemo-functional signal layer and the chemo-functional reference layer are thus identical (thus, also equally thick).

FIGS. 3a, 3b, 4a, 4b, 5a, and 5b show various measuring arrangements (the light waves are drawn in with arrows), wherein in each case at least the in-coupling gratings are illuminated. 3.1 is a waveguide grating structure, 3.2 a lens (a lens system), 3.3 a detector, 3.4 incident light beams, 3.5 reflected light beams, and 3.6 light beams incident on the detector. The illumination may be effected with a (expanded) light beam or with a light strip. The light strip (the light strips) permits (permit) the simultaneous illumination of several waveguide grating structure units arranged in the direction of the light strip (perpendicular to the plane of the drawing). A two-dimensionally expanded light beam permits the simultaneous illumination of two-dimensional arrays of waveguide grating structure units. In the case that the in-coupling gratings have two different x-coordinates on the x-axis (see FIGS. 2b and 2c), the two incident light waves may impinge two different locations of the waveguide grating structure unit (see FIGS. 3b, 4b, and 5b). These two different locations contain, in each case, in-coupling gratings for mode excitation in the (+x)-direction or for mode excitation in the (−x)-direction (see FIGS. 2b and 2c). The incident (or reflected) light waves may be plane waves (represented as arrows with three lines perpendicular thereto) or (slightly) converging (or diverging) waves.

Figure 3B:
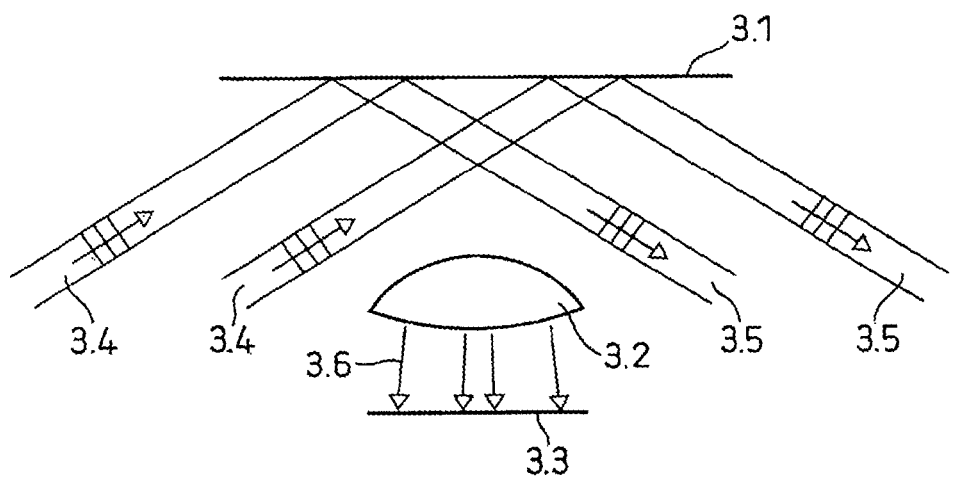
Figure 4A:
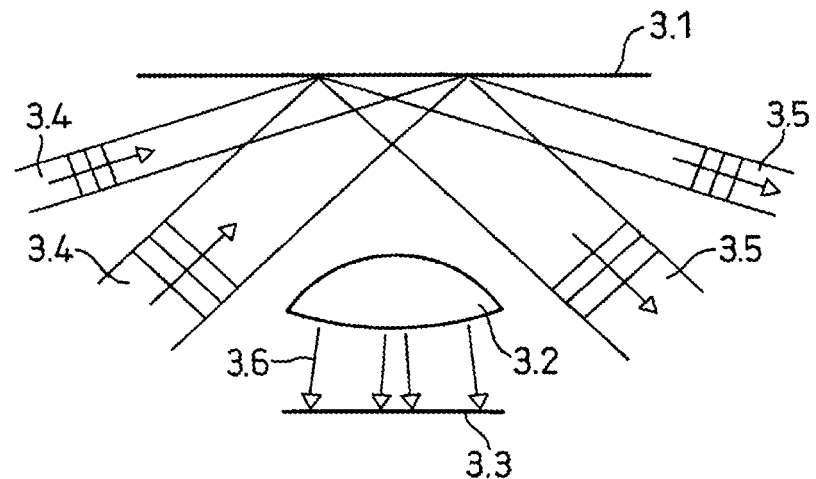
Figure 4B:
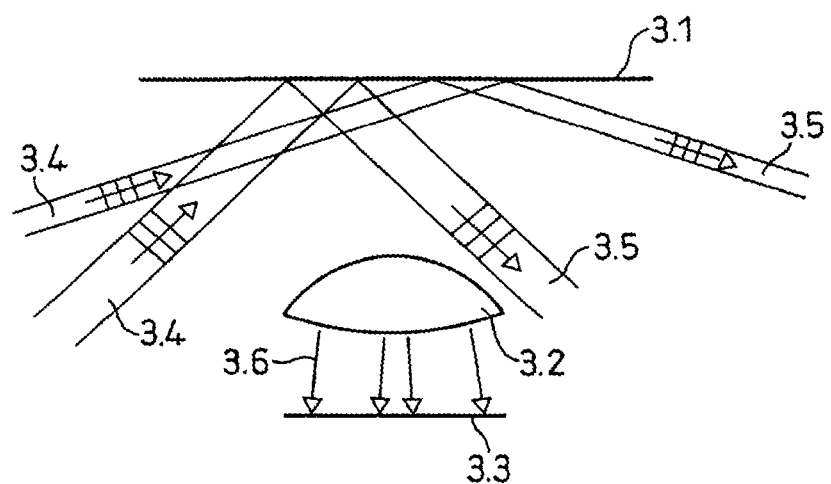
Figure 5A:
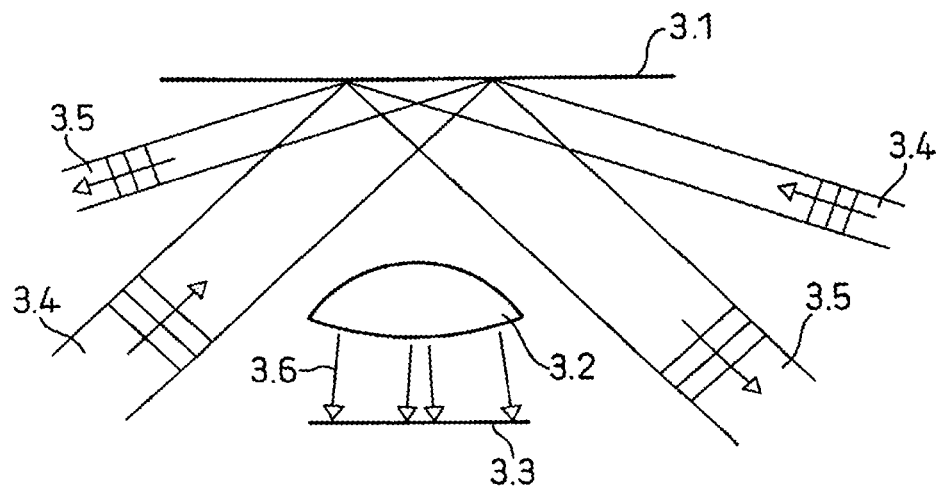
Figure 5B:
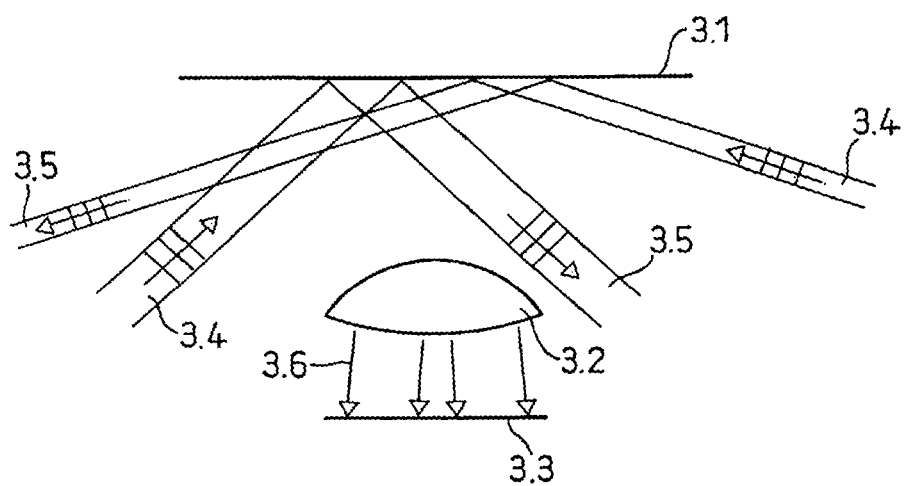

In FIGS. 3b, 4a, and 4b the two incident light waves illuminate the waveguide grating structure from the left and below. In FIG. 3b the two angles of incidence are equal, in the FIGS. 4a and 4b the two angles of incidence are different. In FIGS. 5a and 5b the one incident light wave illuminates the waveguide grating structure from the left and below, the second incident light wave illuminates the waveguide grating structure from the right and below, wherein the two angles of incidence are different in their magnitude.

Common to the FIGS. 3a, 3b, 4a, 4b, 5a, and 5b is the fact that in each case there exist four out-coupled light waves, which arise by the out-coupling of the modes TE+, TM+, TE−, TM−. The four light waves are focussed with one lens or with several lenses, wherein the focuses of the out-coupled light waves do not necessarily have to lie on the one-dimensional or two-dimensional detector surface. A light spot on a pixel array detector should indeed show a certain extension and not only illuminate one pixel. The four beams are in each case drawn in schematically as four arrows. The sequence of the beams is fixed by the grating periods. The light waves of several waveguide grating structure units may also be brought onto a single one-(two)dimensional pixel array detector with one (or more) lens(es) or with a lens system.

The waveguide grating structures (one-(two)dimensional arrays of waveguide grating structure units) described in the PCT applications PCT/EP94/02361 and PCT/CH98/00389 may likewise be read out with a single one-dimensional or two-dimensional pixel array detector in that the out-coupled or radiated light fields, by way of a suitable selection of grating periods or of the lens systems located between the waveguide and detector, are incident onto an array of detectors (see also further below).

It is also advantageous if the light beams, singly or commonly, are guided in tubes, rods, blocks or drilled blocks (beam path is in the bore) and protected in this way. Glass, zerodur, plastics as well as glass-like materials are suitable for the rods and blocks. The perturbations as a result of temperature and/or air fluctuations (air turbulences) may be reduced and, thus, the measurement accuracy increased by way of a protected beam path. These protective devices may also be used with the arrangements as they are described in PCT/EP94/02361 and PCT/CH98/00389.

The incident light beams are preferably linearly polarized below 45 degrees so that the light beams (or light strips) may excite TE-modes as well as TM-modes. The incident light beams may illuminate only the in-coupling gratings, but also the whole waveguide grating structure. The grating periods of the in-coupling gratings and the incident angles are co-ordinated to one another such that in each case a mode excitation occurs. The in-coupling gratings are designed such that the light may be in-coupled from a larger angle segment.

Even if the waveguide grating structure is displaced a little with respect to the incident light waves in the (x,y)-plane, this has (almost) no influence on the measurement since the light spot distributions or (relative) light spot positions may be determined and these are not dependent on the intensity. Since in the out-coupling angle scanning mode it is essentially a matter of the relative position of the (four) light spots on the array of detectors, a slight tilting of the sensor chip with respect to the measuring arrangement has (almost) no influence on the relative position of the light spots and thus (almost) no influence on the measurement result.

In FIGS. 3a, 3b, 4a, and 4b one or two light waves from below and left are incident onto the waveguide grating structure and produce the modes TE+, TE−, TM+, TM−. By way of a suitable selection of the grating period, with a light wave incident in such a manner it is indeed also possible to excite the modes TE− and TM−.

There are also the following alternatives to FIGS. 3a, 3b, 4a, 4b, 5a, and 5b: The incident light beams come almost perpendicularly from below, thus have a small in-coupling angle (with respect to the perpendicular to the waveguide plane), but then the out-coupling angle is considerably larger than the in-coupling angle. The out-coupled light beams are thus incident obliquely downward to the right or obliquely downward to the left or partly obliquely downward to the right and partly obliquely downward to the left onto the one(two)-dimensional detector array(s) (e.g. pixel array detector(s)) (with focussing optics). The out-coupled light waves again illuminate various locations of the detector array, which is achieved by way of a suitable selection of the grating periods.

The position of a light spot (positions of several light spots) may not only be determined with only one one(two)-dimensional pixel array detector (e.g. CCD array, photodiode array or CMOS array) but also in a different manner, for example with (a one(two)-dimensional array of) position-sensitive detector(s) (PSD). Pixel array detectors and PSD may, however, also measure intensities.

Statistical and averaging methods may be carried out with pixel array detectors and position sensitive detectors in that the detectors are read out several times. This method increases the measurement accuracy.

The sensor signals (+−)(ΔN(TE+)−ΔN(TM+)) and (+−)Δ(TE−))−ΔN(TM−)) do not represent temperature-compensated sensor signals and as a result of the subtraction, furthermore display a lower sensitivity than the referenced sensor signals ΔN(TE) and ΔN(TM) equipped with a higher sensitivity (or for example (changes of) the out-coupling angle).

The measurement of four modes likewise permits an improved compensation of temperature drift or pore drift. The various algorithms that are applied are described in the PCT application PCT/CH98/00389. For example, the change of the layer thickness of the wave-guiding film (in the three-layer waveguide model) or the change of the (total) layer thickness of the adlayer (chemo-functional layer plus bonding layer) may serve as a measurement signal. One may operate with one or with several wavelengths.

With the present waveguide grating structures, as already described in the PCT application PCT/CH98/00389, fluorescence, luminescence, chemoluminescence and phosphorescence measurements may be carried out. These, likewise, represent largely temperature-independent measurements. For example, for the direct sensing the same wavelength may be taken as for the fluorescence or luminescence excitation. However, for the direct sensing and for the fluorescence or luminescence excitation one may also apply various wavelengths. With marking measurement (for example, fluorescence, luminescence, etc.), a wavelength filter that only lets through the marking light (e.g. fluorescence light, luminescence light etc) is located in front of the detector.

The fluorescence or luminescence signal may be detected with one or more detectors or with a pixel array detector (where appropriate with imaging optics or with an array of imaging optics). For example, below the waveguide grating structure the measurement head for the detection of the marking and the measurement head for the marking-free detection may be exchanged, however one may merely change or exchange the lens system and remove the wavelength filter that is required for the detection of the marking.

Another measurement method is based on a scattered light measurement in the wavelength scanning mode (see also further below) or in the incident angle scanning mode (see also further below), wherein the scattered light of the waveguide grating structure unit(s) by way of a lens or a lens system is imaged onto a one-dimensional or two-dimensional array of detectors (e.g. on a pixel array detector) and measured during a scanning procedure. The scanning procedures may be repeated.

With the wavelength scanning mode the wavelength of the incident (expanded) light fields (of the incident expanded light beam) is continuously tuned at a fixed angle of incidence and scattered light pictures of the waveguide grating structure are recorded as a function of the wavelength. At the same time, for example, the wavelength may change at a temporally constant rate, while parallel to this (synchronously) one may record (and read out) the scattered light pictures at a constant rate. With the wavelength scanning the grating in-coupling for the respective grating is effected at a certain wavelength (the in-coupling condition is fulfilled) and the scattered light increases markedly. With wavelength scanning the scattered light intensity runs through a resonance during the grating in-coupling. That wavelength (=resonance wavelength), which corresponds to the (weighted) resonance maximum, is determined with or without the use of center of intensity algorithms. The binding (mass coverage) may be deduced from the shifting of the wavelength for mode excitation. The resonance wavelengths for the various in-coupling gratings are generally different (but may also coincide) for reducing crosstalk.

Since the sensitivity for the mass coverage (addition of an additional layer) is dependent on the wavelength, this dependency where appropriate may likewise be taken into account mathematically on evaluation.

A tunable laser (or a tunable laser diode or tunable VCSEL) may be used as a light source (radiation source). Further tunable light sources are mentioned in the section "wavelength scanning mode" (see further below). Preferably the wavelengths of all incident light fields are simultaneously equally changed.

FIGS. 3a, 3b, 4a, 4b, 5a, and 5b are now to be understood to the extent that the lens images the scattered light (or the fluorescence (luminescence) light) onto the pixel array detector. With fluorescence measurements, however, in front of the detector one yet requires a wavelength filter in order to block out the scattered light.

The out-coupling gratings of the waveguide grating structure unit(s) with this mode of measurement should preferably not deflect the out-coupled light beams onto the pixel array detector. The out-coupling grating is, for example, identical to the in-coupling grating and connects, for example, directly to the in-coupling grating, from which practically a single grating results from the in-coupling grating and the out-coupling grating. The waveguide may be (need not be) light-absorbing, but may also only have light-absorbing regions between the gratings.

Also, with this measuring mode two waveguide grating structure units may be mutually referenced.

Figure 6:
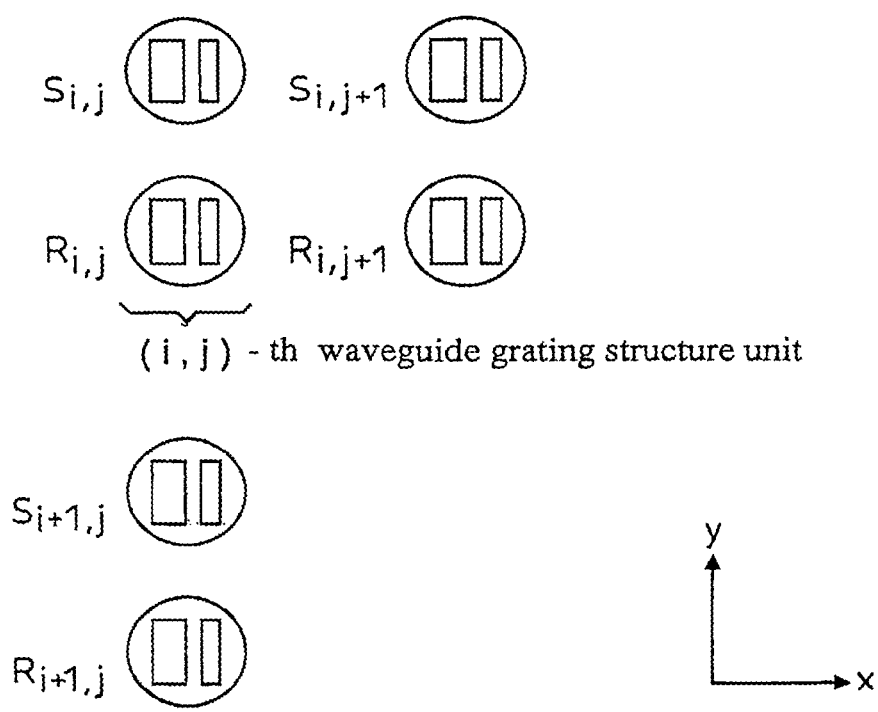

FIG. 6 shows an array of waveguide grating structure units (i, j) consisting of a signal path S(i,j) and a reference path R(i,j). A path contains one in-coupling grating (drawn in as a large rectangle) and one out-coupling grating (drawn in as a small rectangle) with grating lines parallel to the y-axis and a chemo-functional layer (drawn in as a circular surface), which likewise completely occupies the in-coupling grating and the out-coupling grating (or occupies only the in-coupling grating or the out-coupling grating or the region between the in-coupling grating and the out-coupling grating or the whole path). The chemo-functional signal layer is located on the signal path (sensor pad) and the chemo-functional reference layer on the reference path. The reference path R(i,j) may (need not) be present at each waveguide grating structure unit (i, j). The waveguide (the waveguide structure) may (need not) be light-absorbing or may (at least partly) be light-absorbing between two waveguide gratings or between two waveguide grating structure units. The light absorption helps in reducing crosstalk.

FIG. 7 shows an array of waveguide structure units (i,j) consisting of a signal path S(i,j) and of a reference path R(i,j). One path contains a waveguide grating (drawn in as a rectangle) with grating lines parallel to the y-axis and a chemo-functional layer (drawn in as a circular surface), which preferably completely (or also only partly) occupies the waveguide grating (which occupies the path outside the waveguide grating or generally at least partly occupies the path). The chemo-functional signal layer is located on the signal path (sensor pad) and the chemo-functional reference layer on the reference path. The reference path R(i,j) may (need not) be present at each waveguide grating structure unit (i,j). The waveguide structure may be absorbing or may be absorbing at least between two adjacent waveguide grating structure units. The light absorption helps in reducing crosstalk.

Scatter light measurements are also possible in the incident angle scanning mode. The measurement construction for the incident angle scanning mode is described further below. With scattered light measurements, however, by way of a suitable selection of grating periods, one preferably takes care that no diffracted light is incident on the pixel array detector.

With the incident angle scanning mode, in place of continuously tuning the wavelength with a fixed wavelength (or where appropriate with a fixed wavelength distribution), the angle of incidence of the incident (expanded) light beam is continuously tuned angularly. Whilst doing so, the incident (expanded) light beam may angularly change with respect to the fixed waveguide grating structure, or the waveguide grating structure (together with the lens and detection system) may angularly change with respect to the fixed incident (expanded) light beam.

From a waveguide grating structure unit one may also generate only one in-coupling grating (and where appropriate one out-coupling grating) in that all other gratings are provided with the modulation intensity=0. An array of chemo-functional layers may be deposited on the grating, next to the grating or between the gratings. A light strip (an expanded light beam) is in-coupled via the in-coupling grating and the scattered light and/or fluorescence (luminescence) light at the array is measured with an array of detectors or with a pixel array detector (e.g. CCD) with imaging optics. The scattered and/or fluorescence (luminescence) light may, however, also be collected via an array of glass fibers (glass fiber bundles) (with or without attached lenses) with a good light efficiency and be led to an array of detectors (e.g., pixel array detector). The fiber bundles are advantageously arranged in a row. Time-resolved detection permits the measurement of binding procedures.

In the case of scattered light and fluorescence measurements, the measuring head (lens and detector) may carry out both modes. With fluorescence (luminescence) light measurement one still, however, requires a wavelength filter between the waveguide grating structure(s) and the detector.

One may carry out sandwich assays, competition assays, and further multi-step assays with fluorescence technology as well as with scatter light technology. Index-labels (gold globules, metal globules, plastic globules, latex globules, biochemical and biological substances and fragments) may be applied as marking substances in the case of scattered light technology. Apart from direct measurements one may carry out sandwich assays, competition assays, and multi-stage assays with marking-free operation as well as in marking operation. One applies a fluorescence (luminescence) marker with fluorescence measurements (luminescence measurements).

A fluorescence (luminescence) excitation via evanescent waves represents a dissipative effect and may, therefore, be interpreted as a change of the complex effective refractive index (the imaginary part of the complex effective refractive index of the excitation wave changes). The fluorescence measurement, thus, so to speak represents an indirect measurement of the (change in) complex effective refractive index of the excitation wave (or (of the change) of the imaginary part of the complex effective refractive index of the excitation wave).

The marking-free detection may be effected in the (i) wavelength scanning mode, (ii) incident angle scanning mode, and (iii) out-coupling angle scanning mode. The scanning modes are described hereinafter. Measuring techniques that are based on scanning modes are characterised by a high dynamic range.

In (i) and (ii) one effects the passage (continuous tuning) of the scan interval that contains the resonance curve (lowering and/or increase of the measured light intensity as a function of the scanning parameter), preferably continuously (i.e. thus not in a stop-and-go operation). The scanning procedure temporally or via trigger impulses is synchronized with the measurement of the intensity (intensities) of the light field (light fields) carried out by the detector. It is precisely here where it is important for the scanning procedure to take its course with components that are not mechanically moved, for example by the application of a tunable laser diode or a tunable VCSEL or a solid state laser tunable via temperature with the wavelength scanning mode or by way of the application of electro-optical or acousto-optical light beam deflectors with the incident angle scanning mode, since in contrast to mechanical scanning procedures no moved masses are involved. Moved masses create acceleration problems and retard the scanning procedure, which reduces the utilization of the averaging method since per time unit less scans are able to be carried out. With the scanning procedure mostly a start trigger impulse initiates the beginning of the recording of the light fields. Trigger impulses that correlate to the scanning parameter (digital or analog) may trigger further light field recordings during a scanning procedure. However, a purely temporal synchronization is also possible.

With the scanning modes applies one-dimensional or two-dimensional arrays of detectors or arrays of position-sensitive detectors, preferably one-dimensional or two-dimensional pixel array detectors (CCD, photo diode array, CMOS array, etc.) for the detection of the light.

Advantageously, but not absolutely necessarily, radiated light that does not radiate in the direction of the reflected light beam is observed. By way of this the background noise, which arises on account of the reflection of the incident light beam on the lower side of the substrate of the waveguide grating structure and at the liquid surface of the sample, may be reduced. One also does not need to attach any anti-reflection layers on the lower side of the wavelength grating structure. One may also avoid wedge substrates.

The measurement of the radiated, non-reflected light wave (UV, VIS, IR) is effected at the in-coupling grating via a diffraction order which does not correspond to the direction of the reflected light beam, or even via a second grating. The second grating may (need not) have a different grating period than the first grating. The light out-coupling via the second grating may likewise be effected via various diffraction orders.

The measurement of the first diffraction order in reflection also has the advantage that one may operate with smaller grating line numbers. It may also be achieved that the out-coupling efficiency via the second diffraction order is small (e.g., with the in-coupling grating). A sinusoidal (cosinusoidal) grating, for example, has only one plus/minus diffraction order. One may, however, also operate with only one large grating. During a scanning procedure, when coupling in the light, the intensity of the directly diffracted diffraction orders (including the zero-th diffraction order) reduces in reflection and transmission. With the directly diffracted diffraction order the light wave in-coupled firstly via a diffraction order and then out-coupled via a diffraction order is not observed. In particular, with light in-coupling the intensity of the direct (plus/minus) first diffraction order in reflection is reduced. This intensity reduction of the direct (plus/minus) first diffraction order has a resonance character and may be measured in the wavelength scanning mode and in the incident angle scanning mode. The light wave out-coupled via the (minus) second diffraction order is laterally slightly shifted with respect to the direct (plus/minus) first diffraction order (typically by one coupling length). Furthermore, by way of a suitable choice of grating structure it may be achieved that the coupling efficiency of the second diffraction order is small (a sinusoidal grating displays no (plus/minus) second diffraction order). Non-absorbing as well as absorbing waveguides may be applied.

The measurement of the first (second) diffraction order (in reflection) may relate to a (large) uni-diffractive grating but also to a spatial frequency grating of a (large) multi-diffractive grating.

The modulation of at least one grating of a waveguide grating structure unit is preferably selected such that the light coupled-in at a certain waveguide grating structure unit (or sensor location) does not propagate up to the adjacent waveguide structure unit (or sensor location). Thus, crosstalk is tried to be avoided since otherwise, for example, the adjacent waveguide grating structure unit would have a out-coupled or radiated light wave even though light in-coupling does not occur at this adjacent waveguide grating structure unit.

A greater grating modulation has the effect that the in-coupled light is already completely out-coupled over a short stretch of path. At least one grating of the waveguide grating structure unit may be more heavily modulated. Where appropriate, a stop grating (with a greater modulation) or a stop taper or a stop slot may be located between the waveguide grating structure units in each case. The waveguide grating structure unit may consist of a single grating, one or more in-coupling gratings, or one or more out-coupling gratings. The gratings may be uni-diffractive or multi-diffractive. The waveguide grating structure units may also be interconnected and thus, for example, form a large grating. The chemo-sensitive (chemo-functional) layers may then be arranged on a large waveguide grating in a matrix-like manner (without mutually contacting).

FIG. 8 shows an array of sensor units (i,j) consisting of a signal path S(i,j) and of a reference path R(i,j) on a large (uni-diffractive, bi-diffractive or multi-diffractive) waveguide grating with grating lines parallel to the y-axis. With the multi-diffractive grating there are superimposed two, three, four or more different spatial frequency gratings (with the same or with different orientation). A path contains a (bio)chemo-functional layer (drawn in as a small rectangle) which where appropriate covers a distance layer (intermediate layer) (drawn in as a large rectangle). The reference path R(i,j) does not necessarily need to be present at each sensor unit (i,j). The (bio)chemo-functional signal layer is located on the signal path and the (bio)chemo-functional reference layer on the reference path. The waveguide may be light-absorbing, light-absorbing between two sensor locations, or may be non-light-absorbing. The chemo-functional signal layers and intermediate layers may also be circular and/or equally large.

The (chemo-functional) waveguide grating structures shown in the FIGS. 2 to 8 may be applied in all scanning modes. The depositing of the chemo-functional layers is, for example, effected with a spotter, a contact-printing robot, an ink-jet robot, or a liquid handler. The sensor chips may be applied in genomics or proteomics.

With the matrix-like coverage of a large waveguide grating with chemo-functional signal layers (with or without chemo-functional reference layers) preferably grating regions with chemo-sensitive layers have effective refractive indexes different to the effective refractive indexes in grating regions outside the chemo-sensitive layer. This is also to be the case if a passivation layer is present in the grating regions outside the chemo-sensitive layers, in order not to suppress non-specific binding (NSB). At the same time, it is to be ensured that the light in-coupling in the region of the chemo-sensitive layers is effected under another resonance scanning parameter (resonance incidence angle or resonance wavelength) than in the region outside the chemo-sensitive layer, wherein resonance scanning parameters are to be distanced from one another by more than one resonance half-width value, typically several half-width values on the scanning parameter axis. This simplifies the (lateral) identification of the chemo-sensitive layers by the detection system. The thickness of the chemo-sensitive layers may for example be larger (or smaller) than that of the passivation layer. The chemo-sensitive layer may also be seated on an intermediate layer. Or reversely, the passivation layer may also be seated on an intermediate layer. If the thickness of the passivation layer (plus possibly present intermediate layer) is larger than the thickness of the chemo-sensitive layer, the high sensitivity may be ensured for selective bindings at the surface of the chemo-sensitive layer (see FIG. 10). A linker layer (or linker layers) may also be located below the chemo-sensitive layers.

The passivation layer may also be light absorbing. The passivation layer may, for example, be provided with dyes.

The passivation layer does not help in preventing or (significantly) preventing non-specific bonding (NSB). If the reference scanning parameters of the chemo-functional layer and the passivation layer have once been separated from one another, they remain separated from one another since the passivation layer suppresses NSB. During a scanning procedure the two resonance scanning parameters cross on the scanning parameter axis at different times, which helps to reduce crosstalk.

Without the passivation layer NSB occurs and, in the course of a measurement, a coinciding of the two resonance scanning parameters (resonance scanning parameter in the (waveguide grating) region with the chemo-functional signal layer and resonance scanning parameter in the (waveguide grating) region without the chemo-functional signal layer) may occur on the scanning parameter axis, even if initially the effective refractive index in the region of the chemo-functional signal layer is greater than that in the region outside the chemo-functional signal layer. These considerations are also valid for the case that one considers the chemo-functional reference layer instead of the chemo-functional signal layer. If the two resonance scanning parameters temporally coincide with a scanning procedure, light couples more or less at the same time across (in the example of a large waveguide) from a region without a chemo-functional signal layer into a (subsequent) region with a chemo-functional signal layer and from a region with a chemo-functional signal layer into a (subsequent) region without a chemo-functional signal layer, which leads to a disruption of the resonance curves (location-dependent resonance curve(s) that is (are) allocated to the region with chemo-functional signal layer, and location-dependent resonance curve(s) that is (are) allocated to the region without a chemo-functional signal layer) recorded by the detector in a locally resolved manner, and this leads to crosstalk. As a result of the cross-coupling of the light, the resonance curves (e.g. maximum or minimum), which, for example, correspond to the region with the chemo-functional signal layer, are no longer quite so distinctive. A deformation of the resonance curve may occur.

The cross-coupling on a large waveguide grating, i.e. light in-coupling and subsequent light out-coupling, are typically shifted to one another by a coupling length, since in-coupling the mode must firstly be "built up".

Regions that are of interest with regard to measuring technology are—in the mode propagation direction—the transition from a region without a chemo-functional signal layer into the region with a chemo-functional signal layer or the first or first several coupling lengths in the mode propagation direction after the transition (=region I) and—in the mode propagation direction—the transition from a region with a chemo-functional signal layer into the region without a chemo-functional signal layer or the first or first several coupling lengths in the mode propagation direction after the transition (region III). The region II is defined between both transitions. Transitions in the direction of mode propagation (i.e., the extension of the edge of the chemo-functional signal layer) should be as step-like as possible, but preferably significantly smaller than the coupling length. For example, with a spotter one may create chemo-functional signal layers with quite clearly defined transitions. This is important for measurements of the regions I and III. The distance between two chemo-functional signal layers in the mode propagation direction is typically one or more coupling lengths. In the region I, with mode excitation in the region of the chemo-functional signal layer a weakening of light in the directly diffracted diffraction order occurs as long as no cross-coupling takes place. In region III, with mode excitation in the region of the chemo-functional signal layer (without taking interference into account) a light increase (generally: light change)(in the direction of the directly diffracted diffraction order) occurs since a cross-coupling takes place. In the region II, with a mode excitation cross-coupling occurs and the degree of light change (in the direction of the directly diffracted diffraction order) depends on the light absorption coefficient of the waveguide, on the diffraction efficiencies (or on the grating shapes), and on interference parameters. One may measure the light intensities of region I or II or III or of two regions or of all three regions. The lateral shifting of the center of intensity of the light at resonance may be measured. This, in particular, may be of interest if the extension of the chemo-functional signal layer in the direction of mode propagation is only one or a couple of coupling lengths.

If the resonance scanning parameter for the waveguide grating region with the chemo-functional signal layer and the resonance scanning parameter for the waveguide grating region without chemo-functional signal layer remain distanced from one another on the scanning parameter axis by at least one or more resonance half-value widths, then this contribution to crosstalk may be reduced (avoided). Then in the region I a light reduction and in the region II a light increase (without taking interference into account) occurs. In the mode propagation direction an extension of the chemo-functional signal layer by one or a couple of coupling lengths is sufficient for the detection of the light reduction.

If the cross-coupling of the light into the region with chemo-functional signal layer (=region I) is not effected at the point in time in which the resonance curve of the region with chemo-functional layer is just measured, then the perturbation is not very large, since in principle in the region of the chemo-functional signal layer a sidespeak lying outside the resonance curve occurs and this may be blanked out when determining the resonance scanning parameter (the resonance position).

If no passivation layer is present (thus NSB may occur), the thickness of the chemo-functional layer (or the total thickness of the chemo-functional layer and the intermediate layer) should be selected such that the resonance scanning parameter of the two regions (region with and without chemo-functional layer) are always separated from one another on the scanning parameter axis by one or more resonance half-value widths. The resonance width is inversely proportional to the coupling length. An intense grating modulation or light absorption in the waveguide shortens the coupling lengths and increase the resonance (half-value) width.

The above considerations are particularly important if the region with the chemo-functional layer in the mode propagation direction has an extension of one or a couple of coupling lengths or the measurement (also with greater extensions) in the mode propagation direction in the region of the first or first couple of coupling lengths is carried out after the edging of the chemo-functional signal layer. The distance of two chemo-functional signal layers in the mode propagation direction is typically also one or more (typically 1 to 10 or 1 to 100) coupling lengths. Chemo-functional signal layers with an extension of only one or a couple of coupling length(s) lead to greater compacted arrays.

With a larger extension of the chemo-functional layer on a large waveguide grating, the directly diffracted diffraction order superimposes with the out-coupled diffraction order after approximately one coupling length in the mode propagation direction. The diffraction efficiency for the various diffraction orders and interference parameters determine how greatly the resonance is pronounced. One may, for example, make sure that the out-coupled diffraction order is very weak. A larger extension of the chemo-functional layer on the waveguide grating with the same imaging enlargement corresponds to a larger area on the pixel array detector. Therefore, for example, the light intensity of a larger number of pixels may be averaged or a resonance curve may be recorded from a greater number of pixels in each case. In the latter case, either the resonance curves may firstly be averaged and then the resonance scanning parameter determined or firstly one may determine the resonance scanning parameter from each resonance curve and subsequently the resonance scanning parameters may be averaged.

The passivation layer may also be construed as a chemo-functional reference layer that encloses the chemo-functional sensor layer. With a different thickness of the passivation layer and of the chemo-functional signal layer one may (should) take into account the different sensitivities (see FIGS. 9 and 10).

There also exists the possibility of firstly covering the sensor chip over the whole surface with a passivation layer and then locally depositing (possibly in the array format) the chemo-sensitive layers (with linker layer) (where appropriate with a spotter). The combination of the passivation layer and the chemo-sensitive layer is always thicker than the passivation layer alone.

There also exists the possibility of firstly depositing the chemo-sensitive layers and subsequently passivating the free regions (regions which are not provided with a chemo-sensitive layer). The sensor chip may also firstly be provided with a linker layer. The passivation material may be deposited on the whole sensor chip but, however, only adheres to the free regions. In particular, the passivation layer does not cover the binding locations of the chemo-sensitive layer or may at least be washed away.

Markings or windows, which are attached on the sensor, chip and which, for example, are imaged onto a pixel array detector with lens optics may also be used for identification of the chemo-sensitive layers.

However, a non-transparent (or light-absorbing) layer (e.g. of chromium) with windows may be located on the lower side of the sensor chip or on the waveguiding film (on the interface substrate/waveguiding film or on the interface cover/waveguiding film) or in the waveguide structure. The windows lie opposite the chemo-sensitive layers. A chemo-sensitive layer may (need not) cover at least a whole window. The incident light may impinge the waveguide grating structure through the window. It may also be the case that the substrate or a layer or a layer of the waveguide structure is light-absorbing and comprises transparent windows at certain locations (and possibly also carries the grating structure). There are, for example, photo-sensitive (UV-sensitive, IR-sensitive, VIS-sensitive) substrates and layers (of glass, polymer materials, (e.g. plastics), sol gel materials, ormoceres) whose transparency may be structured.

The non-transparent layer with windows on the lower side of the sensor chip (waveguide grating structure) may also be present as a foil (adhesed on or adhering only by way of adhesion forces) or be manufactured by screen printing or vaporization with a diaphragm device that defines the window positions, or also by way of photo-lithography. In this case the substrate should be on the thin side (e.g. 0.1 mm to 1 mm).

The light radiated outside the window is absorbed by the non-transparent layer (by the substrate) and/or the guided wave is damped by this layer or by the (partly) light-absorbing substrate. The extension of a window in the mode propagation direction is typically one or more coupling lengths (may however also be smaller than one coupling length). The waveguide grating structure may (need not) be a large waveguide grating.

Basically, the plane of the non-transparent layer with the windows may be imaged onto the detection plane.

The substrate may also be grated in a reliefed manner similar to an extremely coarse grating (not diffraction grating). This extremely coarse grating may, for example, be a rectangular grating. The actual waveguide grating structure is located at least partly in the troughs (lower level) or at least partly on the projections (upper level) or at least partly on both levels. For the guided light wave this coarse screen acts as a stopper of the wave guiding.

Measurements that are carried out in the scanning mode are largely insensitive to small tiltings and bendings in the case that the waveguide grating structure apart from a sensor pad comprises a reference path. In this case, the referenced sensor signal is the difference of the sensor signal and the reference signal. This difference remains (largely) constant with a small tilting of the waveguide grating structure.

The grating periods of the in-coupling grating(s) and the out-coupling grating(s) may be selected such that the in-coupling and out-coupling is only effected via the first diffraction order. However, the second diffraction order may also be present with the in-coupling grating and/or out-coupling grating. The grating periods of the in-coupling grating and out-coupling grating are equal or different. If the grating periods are equal, the considerations are analogous as with a large waveguide grating where there are grating regions with a chemo-functional signal layer and grating regions (with the same grating periods) without a chemo-functional signal layer. With mode excitation in the wavelength scanning mode or in the incident angle scanning mode, the light reduction is measured at the in-coupling filter and/or the light increase is measured at the out-coupling grating. It may, however, also be the case that the light out-coupled at the out-coupling grating does not impinge the detection device (lens). The out-coupling grating (with a grating period that is equal or different with respect to the in-coupling grating) helps in the reduction of crosstalk. Advantageously, the scanning interval (and the grating periods) is fixed in a manner such that the out-coupling grating during a scan does not act as an in-coupling grating. But even this case may be dealt with since the subsequent in-coupling grating (the next sensor location) then has an out-coupled light beam (and thus light increase). It should, however, be ensured that between the neighbouring sensor locations a resonance overlapping (coinciding of the two resonance scanning parameters) does not occur. This is achieved in that the grating periods of the in-coupling grating and the out-coupling grating are suitably selected and/or the out-coupling grating is not covered with a chemo-functional signal layer or is covered with a passivation layer (the layer thickness difference between the region of the out-coupling grating of a sensor location and the region of the in-coupling grating (with chemo-functional layer)) of the subsequent sensor location should be selected such that no resonance overlapping occurs.

The subsequently described measurements in the wavelength scanning mode or incident angle scanning mode are also possible with a (large) uni-diffractive grating (or with several uni-diffractive gratings) with four (or less) incident (expanded) (where appropriate polarized below 45 degrees with respect to the plane of incidence) light waves for exciting the four modes TE+, TE−, TM+, TM− (chiefly in the base mode m=0), wherein the incidence angle is set such that during a scanning procedure the resonance curves allocated to the modes do not overlap on the scanning parameter axis, i.e. are separated from one another in each case by one or more resonance widths. A possible beam path looks like the following: The beam polarized at 45 degrees impinges onto on the light beam deflector (certainly present in the incident angle scanning mode), subsequently onto a beam expansion optics and then onto a first beam splitter. The two part-beams each impinge on a further beam splitter, wherein then a part beam impinges on the sensor chip and the other part beam firstly on a mirror and then the reflected light on the sensor chip. Thus, four part beams impinge on the sensor chip. It is, however, also possible instead of placing the light beam deflector and/or the beam expanding in front of the first beam splitter, to place these with a fourfold (where appropriate twofold) design in the beam path of the four part beams. If a (large) bi-diffractive grating (if bi-diffractive gratings) are applied, as the case may be, two (expanded) incident light beams polarized at 45 degrees are sufficient. If a (large) multi-diffractive grating (if multi-diffractive gratings) are applied, as the case may be, an incident (expanded) light beam polarized at 45 degrees is likewise sufficient. However, one may also use four incident (expanded) light beams.

The angular separation of the out-coupled light beams (see, e.g., FIGS. 3, 4, and 5) is insignificant in the wavelength scanning mode with resonance curve separation or in the incident angle scanning mode with resonance curve separation.

With a one-dimensional array of waveguide grating structures or sensor locations the waveguide grating structure plane and the detector plane are not parallel to one another.

The scanning modes permit measurements with a large dynamic range. With the introduction of a coarse setting the dynamic range may even be enlarged further (see further below).

With the scanning modes one may apply averaging methods for determining the measurement signal if the measurement signal slightly shifts during the averaging method.

In the wavelength scanning mode (type I), the wavelength of the (expanded) incident light beam (light relates to the visible, infrared, and ultraviolet spectrum) is continuously tuned with a fixed angle of incidence. (The incident light beam should be present, where possible, as a plane wave with a wave vector or as a Gaussian beam with a small as possible divergence). Where appropriate, the angle of incidence may be angularly coarsely preadjusted. However, also (without a light beam deflector) a large scanning interval may firstly be measured (=coarse adjustment) in order subsequently to fix therein a smaller scanning interval that contains the resonance. If for a (chemo-functional) in-coupling grating of a waveguide grating structure unit (or sensor location) at a certain wavelength $\lambda$ (=resonance wavelength) the in-coupling condition $N(\lambda)=n \sin(\alpha)+|I| (\lambda/\Lambda)$ is fulfilled ($N(\lambda)$ =effective refractive index of the mode at wavelength $\lambda$, $\alpha$=in-coupling angle, I=diffraction order, $\Lambda$=grating period, n=refractive index of the air), then a mode excitation occurs and the intensity of the out-coupled or radiated light changes in a resonance-like manner and may be measured with a photo-detector (photo-detector array) as a function of the wavelength. If a chemical reaction or a mass accumulation (e.g., as a result of a (bio)chemical binding) with an effective change in the refractive index $\Delta N$ takes place, then the resonance wavelength $\lambda$ shifts by $\Delta\lambda$ to the new resonance wavelength $\lambda+\Delta\lambda$. For the in-coupling condition the following is now applicable: $N(\lambda+\Delta\lambda)+\Delta N=n \sin(\alpha)+|I| ((\lambda+\Delta\lambda/\Lambda)\Delta\lambda=N(\lambda)+(|I|/\Lambda)\Delta\lambda$. Since in the first order $N(\lambda+\Delta\lambda)=N(\lambda)+(dN(\lambda)/d\lambda)\Delta\lambda$, in the first order the following is applicable $\Delta N= (|I|/\Lambda-dN(\lambda)/d\lambda))\Delta\lambda$, wherein according to the mode equation $dN(\lambda)/d\lambda<0$. The sensitivity $dN(\lambda)/d\lambda$ depends on the polarization and on the mode number of the mode, but also amongst other things on the layer thickness of the waveguiding film (on the layer thicknesses of the waveguide structure), on the refractive indexes of the substrate, of the waveguiding film (of the waveguide layer structure), of the cover, and on the refractive index and layer thickness of the chemo-functional layer. For the referencing with the signal path and with the reference path it is to be noted that the diffraction order I (or |I|) and $dN(\lambda)/d\lambda$ is the same on both paths. Referencing with a thick protective layer (e.g., $SiO_2$) on the reference path is deficient to this extent since $dN(\lambda)/d\lambda$ changes. It is also important for the chemo-functional signal layer and the chemo-functional reference layer to belong to the same class (see section on "compensating disturbances") and/or the two chemo-functional layers to have the same (or almost the same) refractive index and/or the same (or almost the same) layer thickness.

Preferably, but not necessarily, one measures the out-coupled or radiated light wave which does not propagate in the direction of the reflected beam. By way of this the background noise may be reduced.

If one measures with a perpendicular incident light (angle of incidence=0 degrees) and in the direction of the reflected light, the out-coupled or radiated light wave is led via a beam splitter before it (via the lens system) impinges the detector or the detector array. This beam splitter (rear side of the part-transparent layer) may also serve as a beam splitter for producing the incident reference beam.

A lens system may be located between waveguide grating structure and photo-detector. If several waveguide grating structure units are present on the sensor chip, then the intensities of the various out-coupled or radiated light waves with a one(two)-dimensional array of photo detectors (with or without attached fiber bundle) are measured. The lens system that, where appropriate, is located between the sensor chip and the array of photo-detectors may be a one-dimensional or two-dimensional array of lenses (or lens systems), but may also be only one large lens system (a large lens).

The grating periods and/or orientation of the gratings of a waveguide grating structure and/or position of the lens system are selected such that one photo-detector measures the intensity of an out-coupled radiated light wave in each case. The photo-detector may, in turn, consist of smaller individual detectors, wherein however always only the intensity of an out-coupled or radiated light wave is of interest. The smaller individual detectors of the various photo-detectors may be grouped together forming a one(two)-dimensional pixel array.

The lens array(s) (spherical or cylindrical lens) located between the sensor chip and the detector, where appropriate, may also serve as an array of (almost) Fourier lenses, since with this intensities too may be measured as long as the fields of light do not superimpose. The (almost) Fourier plane forms the detector plane or may be imaged onto the detector via lens optics.

Between the sensor chip and the detector there may also be located a fiber bundle or a system of fiber bundles (possibly with a deposited lens system or lens array), which measures the radiated or out-coupled light or the scatter light of the excited modes. Advantageously, the fiber bundle is arranged in a row.

A tunable light source (tunable laser, tunable laser diode, tunable VCSEL (vertical cavity surface emitting laser) (where appropriate in single mode operation), a white light source with (continuously tunable) monochromator (prism monochromator, grating monochromator), a white light source with (continuously tunable) Fabry-Perot interferometer, etc., is applied in the wavelength scanning mode (type I). As tunable light sources, where appropriate, single mode laser light sources may be applied. The light sources may contain collimation optics. Monochromators with electro-optical (EO) or acousto-optical (AO) components (such as, e.g., EO or AO light beam deflectors, EO or AO Bragg gratings, etc.) are scanning devices without moving mechanics.

One produces an expanded light beam with white light sources in that preferably firstly the light source is imaged onto a hole aperture and subsequently is expanded via a lens, wherein the distance hole aperture—lens corresponds to the focal length of the lens. The expansion may be effected one-dimensionally (using (crossed) cylinder lenses) or two-dimensionally (using spherical lenses or crossed cylinder lenses).

With laser light sources with a small divergence one employs a beam expander (two spherical lenses of differing focal length or two cylinder lenses of different focal length or two crossed pairs in each case of two cylinder lenses of differing focal length) for producing a (one-dimensional or two-dimensional) expanded light beam.

It is advantageous if the expanded light beam simulates a plane wave as well as possible, and thus is neither convergent nor divergent.

The light sources may be unpolarized or polarized (linear, circular). By rotating a linearly polarized laser about the laser axis one may produce, for example, 45 degree linearly polarized light (with respect to the plane of incidence). Linearly polarized light may also be produced in a polarizer.

Several wavelength scans may be carried out very quickly one after another and be subjected to a statistical averaging method. A resonance curve results from a wavelength scan and, from this, one determines the resonance wavelength. These resonance wavelengths are then subjected to an averaging method. Typically 10, 100, or 1000, etc., wavelength scans are carried out per second or per time unit and subjected to an averaging method. The averaging methods increase the measuring accuracy. Tunable lasers or tunable laser diodes or VCSELs permit a rapid continuous tuning (scan) of the wavelength, since (in the case that) the matching is effected without the application of movable mechanics.

A beam splitter (part-transparent layer, glass plate, diffraction grating, etc.) may be located in the incident light beam before or after the beam expansion, in order on a 1(2)-dimensional position-and intensity-sensitive detector (e.g., pixel array detector) (=reference detector), where appropriate provided with a reducer or with employing a beam compressor or beam expander (or a imaging optics), to take into account the beam stirring and the intensity fluctuations of the incident light beam in the form of a reference signal. A grating beam splitter (in the first and higher order of diffraction) furthermore has the advantage that, with this one, may observe wavelength fluctuations on the reference detector that do not correspond to the actual scanning procedure.

For example, the beam stirring may be observed via a normal beam splitter (for example, beam splitting cube) and wavelength fluctuations (including beam stirring) may be observed via a grating beam splitter. By way of this one may separate the beam stirring and the fluctuation of the wavelength from one another. One may employ one or two reference detectors (with one or more beam shaper optics). Both light fields may be incident on a pixel array detector next to one another. Instead of the use of a normal beam splitter and a grating beam splitter, the zero-th and a higher diffraction order may be measured with a single grating beam splitter. The zero-th (reflector) diffraction order at the same time assumes the function of the normal beam splitter (see also section "incident angle scanning mode").

During a wavelength scan in principle a displacement $\Delta x(t)$ of the (expanded) light beam (or of the light center of intensity) as a function of the wavelength scanning parameter t should not occur on the reference detector. Thus, it should be the case of $\Delta x(t)=0$.

The continuous tuning of the wavelength $\lambda$ is achieved via the change of the wavelength scanning parameter t. The wavelength $\lambda(t)$ is thus a function (mostly a linear function) of the wavelength scanning parameter t. With a wavelength scan the wavelength scanning parameter t runs through a certain interval $(t_{start}, t_{end})$ and is subsequently traversed back so that a new wavelength scan may be started again.

If beam stirring occurs during the scanning procedures, then on the reference detector the shifting $\Delta x(t)$ is not equal to zero at least temporarily, which corresponds to an angular shifting $\Delta \alpha(t)$ of the fixed angle of incidence $\alpha$. In the first order there applies $\Delta x(t)=L\Delta\alpha(t)$, wherein in the case of a normal beam splitter, L is the beam length between the light source (beam pinch off) and the reference detector.

The beam stirring is assumed to be constant during a scanning passage in an evaluation method. One may measure the beam stirring before and/or after a scanning passage or one may form an average value from several angle changes $\Delta\alpha$ caused during a scanning passage on account of beam stirring. The angular perturbation $\Delta\alpha$ creates a wavelength shifting (perturbation) $\Delta\lambda^{perturbation}$, since because $dN/d\lambda<0$ at $\alpha+\Delta\alpha$, the coupling equation $N(\lambda_{res}(\alpha)+\Delta\lambda^{perturbation})=n \sin(\alpha+\Delta\alpha)+(1/\Lambda)(\lambda_{res}(\alpha)+\Delta\lambda^{perturbation})$ may only be fulfilled if also the wavelength $\lambda_{res}(\alpha+\Delta\alpha)=\lambda_{res}(\alpha)+\Delta\lambda^{perturbation}$ changes. From the experimental resonance curve, which corresponds to the in-coupling equation $N(\lambda_{res}(\alpha)+\Delta\lambda^{perturbation})=n \sin(\alpha+\Delta\alpha)+(1/\Lambda(\lambda_{res}(\alpha)+\Delta\lambda^{perturbation})$, one determines the resonance wavelength $\lambda_{res}(\alpha+\Delta\alpha)=\lambda_{res}(\alpha)+\Delta\lambda^{perturbation}$ by way of a Fit algorithm (e.g., center of intensity algorithm). With $N(\lambda_{res}(\alpha)+\Delta\lambda^{perturbation})=N(\lambda_{res}(\alpha))+(dN/d\lambda)\Delta\lambda^{perturbation}$ and $N(\lambda_{res}(\alpha))=n \sin(\alpha)+(1/\Lambda)\lambda_{res}(\alpha)$ there results $(dN/d\lambda-1/\Lambda)\Delta\lambda^{perturbation}=n \sin(\alpha+\Delta\alpha)-n \sin(\alpha)$. If $N(\lambda)$ (or $dN/d\lambda$) is known from the mode equation or from a calibration curve, one may compute $\Delta\lambda^{perturbation}$ and thus $\lambda_{res}(\alpha)$. The corrected (with respect to the angle of incidence $\alpha$) resonance wavelength is thus $\lambda_{res}^{corr}=\lambda_{res}(\alpha+\Delta\alpha)-\Delta\lambda^{perturbation}=\lambda_{res}(\alpha)$.

Apart from beam stirring wavelength fluctuations $\Delta\lambda^{perturbation}=\Delta\lambda^{wavelength\ shift}$ may also occur, which do not correspond to the actual wavelength scanning procedure. The correct (corrected) resonance wavelength is again $\lambda_{res}^{corr}=\lambda_{res}-\Delta\lambda^{perturbation}$, wherein $\lambda_{res}$ represents the measured resonance wavelength. If several perturbations occur, then there applies $\lambda_{res}^{corr}=\lambda_{res}-\Sigma_i\Delta\lambda^{perturbation\ i}$, wherein perturbation i is to mean the ith perturbation.

In another evaluation method with respect to the compensation of beam stirring, one measures the out-coupled or radiated intensity as a function of the wavelength $\lambda(t,\alpha)=\lambda(t,\alpha+\Delta\alpha(t))-\Delta\lambda^{perturbation}(t)$ $(\lambda(t,\alpha+\Delta\alpha(t))=\lambda(t))$ with a photodetector (photo detector array), and from this the corrected resonance $\lambda_{res}^{corrected}$ is evaluated with a Fit algorithm, wherein the perturbation $\Delta\lambda^{perturbation}(t)$ is determined by way of $\Delta\alpha(t)=\Delta x(t)/L$ and the grating diffraction equation of the in-coupling grating. In place of beam stirring $\Delta\alpha(t)$, the perturbation according to the grating diffraction equation is to be effected via a wavelength change $\Delta\lambda^{perturbation}(t)$, wherein the grating period and the diffraction order of the in-coupling grating are to be substituted into the grating diffraction equation. There applies $\sin(\alpha+\Delta\alpha(t))=\sin(\alpha)+(1/\Lambda)\Delta\lambda^{perturbation}(t)$, from which one may compute $\Delta\lambda^{perturbation}(t)$ in dependence on $\Delta\alpha(t)$. $\Delta x(t)$ is measured by the reference detector. This evaluation method may likewise be extended to several perturbations, i.e. the following is applicable: $\lambda(t,\alpha)=\lambda(t,\alpha+\Delta\alpha(t))-\Sigma_i\Delta\lambda^{perturbation\ i}(t)$, wherein perturbation i indicates the ith perturbation. It is also possible to assume the perturbation(s) as constant during the scanning procedure in that the disturbance(s) are measured before and/or after the scanning procedure and/or during the scanning procedure (as an average value). For determining the resonance, the intensity as the function of λ(t,α) is evaluated.

Also a start error in the wavelength scanning parameter t (t runs through the interval ($t_{start}$, $t_{end}$)) may be compensated as follows: By way of the fact that the sensor pad and the signal path may be measured parallelly at the same time, the start error on both paths is the same and may therefore be referenced away. The referenced (registered as a function of time) measurement signal is $\lambda_{res}^{ref} = \lambda_{res}^{signal\ path} - \lambda_{res}^{reference\ path}$, wherein $\lambda_{res}^{signal\ path}$ represents the resonance wavelength for the signal path and $\lambda_{res}^{reference\ path}$ the resonance wavelength for the reference path.

On working with a reference path located on the sensor chip where appropriate one may also do away with the evaluation of the corrected wavelengths $\lambda_{res}^{corr}$ as long as the perturbations on the signal path and on the reference path are equal and, thus, may be referenced away.

In the wavelength scanning mode (type II), in contrast to the wavelength scanning mode (type I), the scanning element is located on the detection side, i.e. in the beam path of the light field radiated or out-coupled by the waveguide grating structure. The scanning element is, for example, a monochromator or a scanning Fabry-Perot interferometer. In the wavelength scanning mode (type II) one applies a white light source (broadband light source) with a one-dimensional or two-dimensional beam expansion. The waveguide grating structure is illuminated at a fixed angle. Where appropriate (but not necessarily), the incident light beam may be angularly coarsely preadjusted with a light beam deflector.

By way of a beam splitter (beam splitter cube) and where appropriate a beam expander (or beam compressor), the beam quality (locally resolved), intensity fluctuations, (angular) beam shifts, etc.) may be detected (locally resolved) on a second pixel array detector (CCD, CCD-camera, photodiode array, CMOS-array, etc.) and referenced with the sensor signal (locally resolved).

A lens system or an array of lens systems and a scanning element (where appropriate with the associated optics) are located between the waveguide grating structure (with or without absorbing waveguide) and the pixel array detector. The waveguide grating structure and the detection surface are preferably parallel to one another. The lens system may act as an imaging lens or almost imaging lens. The lens system may also consist of two lenses and the scanning Fabry Perot interferometer may also be located between the two lenses.

With a perpendicular incidence of light the out-coupled or radiated light is firstly led via a beam splitter. The rear side of this beam splitter may serve as a beam splitter for producing the incident reference beam.

The transmission wavelength of the scanning element changes on continuously tuning the scanning element as a function of the scanning parameter t. If the transmission wavelength corresponds to the resonance wavelength at which mode excitation occurs at a certain sensor pad (signal path or reference path) of a waveguide grating structure unit, then on the pixel array detector the light distribution changes at that location that corresponds to the sensor pad. The changes of the light distribution (light reduction, light intensification, light center of intensity shifting within a defined detection region) as a function of the transmission wavelength run through a resonance. The evaluations are effected as with the wavelength scanning mode (type I).

In the incident angle scanning mode the angle of incidence of the expanded incident light beam (light relates to the visible, but also ultraviolet and infrared spectrum) is continuously tuned at a fixed wavelength with the help of a light beam deflector. The incident light beam should advantageously be present as a plane wave with a wave vector (with as small as possible divergence) or as a Gaussian beam with as small as possible divergence.

The advantage of the in-coupling angle scanning mode with respect to the wavelength scanning mode with a tunable laser source is the availability of laser light sources of fixed wavelength in the green/blue, dark blue, and ultraviolet wavelength region. Tunable laser light sources in this wavelength region are practically not economically obtainable. Shorter wavelengths increase the sensitivity of the waveguide grating structure (see Thin Solid Films 126 (1985), 205-211). Furthermore, in the shorter-waved region the light absorption of the waveguide increases and where necessary need not be incorporated.

Mechanical, galvanometric, vibrating, rotating, electro-optical (EO), or acousto-optical (AO) light beam deflectors (scanners) may be used. Mechanical deflectors are, for example, rotating or vibrating mirrors, polygonal mirrors, or camera wedges. Where appropriate the angle of incidence interval to be continuously tuned is angularly coarsely pre-adjusted with a second light beam deflector, wherein the second light beam deflector may be located in front of or after the first light beam deflector. This second light beam deflector responsible for the coarse adjustment may indeed contain mechanically moved components. The coarse preadjustment may, however, also be effected via a wavelength adjustment for which it requires a tunable light source (e.g. tunable laser diode, tunable VCSEL). The light beam expansion may be effected before or after the light beam deflector(s). The waveguide grating structure is not rotated but it streaks the one-dimensionally or two-dimensionally expanded light beam past the array of the waveguide grating structure unit(s) or past the array of sensor locations and, thus, changes the angle of incidence. The waveguide grating structure always remains illuminated during this angular continuous tuning.

Preferably, the light beam deflector is added into the beam path between the light source (or light source with collimation optics) and the beam expansion. The light beam deflector has the effect that the light beam crosses through the beam expansion somewhat obliquely. The arrangement has the effect that a widened light beam may be angularly continuously tuned. The light beam has a Gauss distribution in the case of a laser beam.

Non-mechanical light beam deflectors (such as EO and AO deflectors) have the advantage that they function very rapidly since no movable mechanics are employed for beam deflection, and therefore statistical averaging methods may be used with the measurements. Thus, for example one may carry out several scans rapidly one after another and the in-coupling angles (=resonance angle of incidence) may be computed from the resonance curves. One may then evaluate an average value from these in-coupling angles. Typically 10, 100, or 1000, etc., in-coupling angle evaluations per sensor pad per second or per time unit are carried out and subjected to an averaging method. The averaged reading then forms a weighted measurement point. An averaging method increases the measurement accuracy. Also, the resonance curves may firstly be superimposed (averaged) and then the in-coupling angle determined from the averaged resonance curve. However, the individual values participating in the averaging methods may be constantly recorded. The quantity (or definition region) of the individual values participating in the averaging is then continuously moved on (Example: The oldest reading is not included in the definition region, but instead the next newer reading appears).

If for a sensor pad the in-coupling condition is fulfilled at a certain angle of incidence (=resonance angle of incidence), then a mode excitation occurs and the intensity of the out-coupled or radiated light increases in a resonant-like manner (or the intensity of the directly diffracted diffraction order (e.g., in reflection) reduces in a resonant-like manner) and may be measured as a function of the angle of incidence with a photo-detector (photo detector array). The two regions of the light increase and the light reduction are typically shifted to one another by one coupling length. If one scans through the resonance angle of incidence, then the intensity of the out-coupled light displays a resonance curve with a maximum and the intensity of the directly diffracted diffraction order (in reflection) displays a resonance curve with a minimum. If a mass accumulation (e.g., as a result of a (bio) chemical binding) or a bio(chemical) reaction takes place, then the resonance angle of incidence shifts.

When recording resonance curve(s), the light distribution of the (expanded) incident light beam (e.g., the (projected) Gaussian distribution) shifting locally and temporally on the waveguide grating structure during a scan must be taken into account. The advantage of the incident angle scanning mode is that the sensitivities of the waveguide, which depend on the wavelength, in contrast to the wavelength scanning mode— need not be retrospectively corrected—since the wavelength is constant.

Preferably, but not necessarily—one measures that out-coupled or radiated light wave which does not propagate in the direction of the reflected light beam, which effects a reduction in the background noise.

If one measures at a perpendicular light incidence (angle of incidence=0 degrees) and in the direction of the reflected light, the out-coupled or radiated light wave is led via a beam splitter before it (via a lens system) impinges the detector or detector array. This beam splitter (rear side of the part-transparent layer) may also serve as a beam splitter for producing the incident reference beam.

A lens system may be located between the waveguide grating structure and the photo-detector. If several waveguide grating structure units are present on the sensor chip, then the intensities of the various out-coupled or radiated light waves are measured with a one-dimensional or two-dimensional array of photo-detectors (with or without an attached fiber bundle). The lens system, which, where appropriate, is located between the sensor chip and array of photo-detectors, may be a one-dimensional or two-dimensional array of lenses (or lens systems) or, however, it may only be one large lens system (a large lens).

Grating periods and/or orientation of the gratings of a waveguide grating structure and/or position of the lens system are selected such that in each case one photo detector measures the intensity of the out-coupled or radiated light wave. The photo-detector may in turn also consist of smaller individual detectors, wherein, however, only the intensity (or entire intensity) of an out-coupled or radiated light wave is of interest. The small individual detectors of the various photo-detectors, grouped together, may form a one-dimensional or two-dimensional pixel array detector (photodiode array, CCD array, CMOS array etc.).

The lens array(s) (spherical or cylindrical lens) located between the sensor chip and the detector, where appropriate, may also act as an array of (almost) Fourier lenses (as almost (Fourier) lens) since intensities may also be measured with this as long as the light fields do not superimpose. The (almost) Fourier plane forms the detector plane or may be imaged onto the detector via lens optics.

Between the sensor chip and the detector there may be located a fiber bundle or a system of fiber bundles (possibly with attached lens system or lens array), which measures the radiated or out-coupled light or the scatter light of the excited modes. Advantageously, the fiber bundles are arranged in series.

In the incident angle scanning mode one uses a monochromatic light source (laser with a constant wavelength, laser diode with constant wavelength, VCSEL with constant wavelength, white light source with wavelength filter, white light source with monochromator (e.g. grating monochromator, prism monochromator), white light source with Fabry-Perot interferometer). The light sources may contain collimation optics. Lasers or laser diodes may also be stabilized in frequency. A laser diode is likewise based on the laser effect (i.e., no induced emission takes place).

With white light sources an expanded light beam is produced in that, preferably, firstly the light source is imaged onto a hole aperture and subsequently is widened via a lens, wherein the distance hole aperture—lens corresponds to the focal width of the lens. The expansion may be effected one-dimensionally (using cylinder lenses) or two-dimensionally (using spherical lenses or crossed cylinder lenses).

With laser light sources of a small divergence, for excitation of a (one-dimensionally or two-dimensionally) expanded light beam one employs a beam expander (two spherical lenses of a different focal width or two cylinder lenses of a different focal width or two crossed pairs of in each case two cylinder lenses of a different focal width).

It is advantageous if the expanded light beam simulates a plane wave as well as possible, thus is neither convergent nor divergent.

A beam splitter 11.15 (part-transparent layer, glass plate, diffraction grating etc.) may be located in the incident light beam before or after the beam expansion and/or before or after the light beam deflector in order on a one-dimensional or two-dimensional position-sensitive and intensity-sensitive detector (e.g., pixel array detector) (=reference detector), where appropriate provided with an attenuator 11.17, to take into account the beam stirring and/or the intensity fluctuations of the incident light beam in the form of a reference signal. A beam expander or beam compressor (=anti-expander) 11.16 may also be located between the beam splitter and the reference detector 11.18 in order to adapt the beam diameter to the reference detector 11.18.

A grating beam splitter furthermore has the advantage that with this, on the reference detector, apart from beam stirring and/or intensity fluctuation of the incident light beam one may also observe a wavelength fluctuation of the light source, and the measuring signal may be correspondingly corrected. In this case the plus/minus first or higher diffraction order is observed on the reference detector.

Advantageously—but not absolutely necessarily—the beam splitter(s) between the light source (where appropriate with collimation optics) and the light beam deflector is introduced into the beam path.

If a normal beam splitter (e.g. beam splitter cube, part-transparent mirror) and a grating beam splitter are connected after one another with the application of one or two reference detectors (e.g. one(two)-dimensional PSD, one(two)-dimensional pixel array detectors) where appropriate equipped with beam shaper optics and attenuators then, via the normal beam splitter, one may observe the beam stirring and, via the grating beam splitter, one may observe the combination of beam stirring and wavelength fluctuation with the reference detector(s). From this one may separately determine the beam stirring and wavelength fluctuation. If, specifically, the first shift signal $\Delta x_1$ (=beam stirring) measured via the normal first beam splitter (e.g., beam splitter cube) is subtracted from the second shift signal $\Delta x_2$ (=beam stirring and wavelength fluctuation) measured via the grating beam splitter (second beam splitter), then the second shift signal with the first shift signal referenced shift signal $\Delta x_2 - \Delta x_1$ represents the wavelength fluctuation (notation: bold x indicates vectors). Preferably, the grating lines of the grating beam splitter are perpendicular to the plane of incidence and the lines of a pixel array detector parallel to the plane of incidence. The reference detectors are preferably beamed perpendicularly. Inclined illumination is likewise possible in that a shift $\Delta x$ is projected onto the plane perpendicularly to the beam impinging the reference detector. In this case in the subsequent computations one must not take $\Delta x$ into account but the projected $\Delta x$.

Instead of using two beam splitters, the zero-th and a higher diffraction order may be measured with a grating beam splitter. The zero-th (reflected) diffraction order at the same time assumes the function of the normal beam splitter (e.g., beam splitter cube). Two reference deflectors may be applied, but the zero-th and the higher diffraction order (where appropriate using suitable deflection optics (e.g., mirrors)) may also be incident next to one another separately on only one reference detector. For example, the zero-th (reflected) and a higher (the first reflected) diffraction order may also cross through the same beam expander (compressor) at various angles.

Now and then, for control purposes it is sufficient to only observe the higher diffraction order since with this the additive errors of beam stirring and wavelength fluctuation is measured. However, the errors may compensate. In a coarse approximation the shift signal measured with a reference detector is interpreted as a change in angle.

One may also apply two normal beam splitters. With this, apart from the incident light beam one may generate two part beams. The beam stirring is measured with a (first) part beam. The other (second) part beam impinges onto a (scanning) Fabry-Perot interferometer (with optics) (in transmission and/or reflection) and subsequently onto a detector (intensity detector and/or position-sensitive detector). Thus, the wavelengths (wavelength fluctuation) (and the beam stirring) are measured with this other part beam. Where appropriate the beam stirring may in turn be referenced away. The wavelength fluctuation and the beam stirring may, however, also be recorded as one variable. In this case one does not require the first part beam. The configuration may be applied in the wavelength scanning mode in that, for example, one measures before or after a scanning passage.

The continuous tuning of the angle of incidence $\alpha$ is achieved by way of changing the incident angle scanning parameter t (e.g., electrical signal with an electro-optical light beam deflector). The angle of incidence $\alpha(t)$ is thus a function of the incident angle scanning parameter t. With an incident angle scan the incident angle scanning parameter t runs through a certain interval $(t_{start}, t_{end})$ and subsequently is traversed back so that again one may start a new scan.

In the case of a grating beam splitter (operated in the first or higher diffraction order), a wavelength fluctuation during a scanning procedure effects a displacement $\Delta x(t)$ of the light distribution on the reference detector as a function of the incident angle scanning parameter t. Under the assumption that no beam stirring occurs, from the shifting $\Delta x(t)$ of the light distribution on the reference detector, while evaluating the grating diffraction equation with respect to the grating beam splitter, one may evaluate the change in wavelength $\Delta\lambda(t)$. (The angle change in the first order is $\Delta x/L$, wherein L is the beam distance of the first or higher diffraction order between the grating beam splitter and the reference detector. However, one may also compute exactly).

For the sake of simplicity the subsequent considerations are made for the case in which the grating beam splitter is located between the light source and the light beam deflector. The considerations, however, are also valid for the case in which the grating beam splitter is located between the light beam deflector and the waveguide grating structure. A shifting of the light distribution on the reference detector in this case means the shifting of the light distribution that does not correspond to the actual incident angle scanning procedure. Thus, one means a deviation from the nominal displacement.

In an evaluation method the wavelength fluctuation is assumed to be constant during a scanning passage. The wavelength fluctuation may be measured before and/or after a scanning passage or one may firstly determine the wavelength fluctuations measured during a scanning procedure. The perturbation $\Delta\lambda$ of the wavelength creates a perturbation $\Delta\alpha^{perturbation}$ of the in-coupling angle, since because $dN/d\lambda < 0$ at $\lambda + \Delta\lambda$ the in-coupling equation $N(\lambda + \Delta\lambda) = n \sin(\alpha_{res}(\lambda + \Delta\lambda)) + (l/\Lambda)(\lambda + \Delta\lambda)$ may only be fulfilled if also the in-coupling angle $\alpha_{res}(\lambda + \Delta\lambda) = \alpha_{res}(\lambda) + \Delta\alpha^{perturbation}$ changes. From the experimental resonance curve, which corresponds to the in-coupling equation $N(\lambda + \Delta\lambda) = n \sin(\alpha_{res}(\lambda + \Delta\lambda)) + (l/\Lambda)(\lambda + \Delta\lambda)$, by way of a Fit algorithm (e.g., center of intensity algorithm) the resonance angle of incidence $\alpha_{res}(\lambda + \Delta\lambda) = \alpha_{res}(\lambda) + \Delta\alpha^{perturbation}$ prevailing at $\lambda + \Delta\lambda$ is determined. With $N(\lambda + \Delta\lambda) = N(\lambda) + (dN/d\lambda)\Delta\lambda$ and $N(\lambda) = n \sin(\alpha_{res}(\lambda)) + (l/\Lambda)\lambda$ there results $(dN/d\lambda - l/\Lambda)\Delta\lambda = n \sin(\alpha_{res}(\lambda + \Delta\lambda)) - n \sin(\alpha_{res}(\lambda))$. If $N(\lambda)$ (or $dN/d\lambda$) is known from the mode equation or from a calibration curve, then one may compute $\alpha_{res}(\lambda)$ or $\Delta\alpha^{perturbation}$. The corrected (with respect to the wavelength $\lambda$) in-coupling angle (=resonance angle) is accordingly $\alpha_{res}^{corr} = \alpha_{res}(\lambda + \Delta\lambda) - \Delta\alpha^{perturbation} = \alpha_{res}(\lambda)$.

Apart from wavelength fluctuation, beam stirring $\Delta\alpha^{perturbation} = \Delta\alpha^{beam\ stirring}$ may also occur. The corrected resonance angle of incidence is again $\alpha_{res}^{corr} = \alpha_{res} - \Delta\alpha^{perturbation}$, wherein $\alpha_{res}$ represents the measured resonance angle of incidence. If several perturbations occur, then there is valid $\alpha_{res}^{corr} = \alpha_{res} - \Sigma_i \Delta\alpha^{perturbation\ i}$, wherein perturbation i is the ith perturbation.

In another evaluation method with respect to the compensation of wavelength fluctuation, the out-coupled or radiated intensity as a function of the angle of incidence $\alpha(t,\lambda) = \alpha(t, \lambda + \Delta\lambda(t)) - \Delta\alpha^{perturbation}(t)$ is measured ($\alpha(t,\lambda + \Delta\lambda(t)) = \alpha(t)$) with a photo-detector (photo-detector array) and from this with a Fit algorithm the corrected resonance $\alpha_{res}^{corr}$ is determined, wherein the perturbation $\Delta\alpha^{perturbation}(t)$ is determined via $\Delta\lambda(t)$ and the grating diffraction equation of the in-coupling grating. Instead of wavelength fluctuation $\Delta\lambda(t)$ the perturbation according to the grating diffraction equation is to be effected by an angle change $\Delta\alpha^{perturbation}(t)$, wherein the grating period and the used diffraction order of the in-coupling grating are to be substituted into the grating diffraction equation. There applies $\sin(\alpha(t,\lambda) + \Delta\alpha^{perturbation}(t)) = \sin(\alpha(t,\lambda)) + (l/\Lambda)\Delta\lambda(t)$, from which $\Delta\alpha^{perturbation}(t)$ in dependence on $\Delta\lambda(t)$ may be computed. $\Delta\lambda(t)$ is determined via the $\Delta x(t)$ of the reference detector and via the grating diffraction equation of the grating beam splitter. This evaluation method may likewise be applied to several perturbations, i.e. the following is applicable: $\alpha(t,\lambda) = \alpha(t,\lambda + \Delta\lambda(t)) - \Sigma_i \Delta\alpha^{perturbation\ i}(t)$, wherein perturbation i means the ith perturbation. It is also possible to assume the perturbations as constant during the scanning procedure, in that the perturbations(s) are measured (as an average value) before and/or after the scanning procedure and/or during the scanning procedure. The intensity as a function of $\alpha(t,\lambda)$ is evaluated for determining resonance.

A start error in the angle of incidence scanning parameter t may—as already mentioned with the wavelength scanning mode—be referenced away via the reference path on the sensor chip. On operating with a reference path located on the sensor chip, where appropriate one make do without determining $\alpha_{res}^{corr}$ as long as the perturbations on the signal path and the reference path are equal and, thus, may be referenced away.

In the out-coupling angle scanning mode the angular shifting or local shifting on the detector (and/or intensity change) of the out-coupled (monochromatic) light rays is measured with the help of a one-dimensional or two-dimensional array of (position-sensitive) detectors (e.g. PSD, PSD-array, CCD, CCD camera, photodiode array, CMOS ARRAY etc.), wherein preferably a (spherical and/or cylindrical) lens or lens system is located between the waveguide grating structure unit and the detector. The monochromatic light source is preferably a laser, a laser diode, a VCSEL, etc. The laser light sources are preferably operated in a mono-mode manner or stabilized in frequency.

Since no movable mechanics are involved in the measuring procedure, the out-coupling angle scanning mode is particularly well suited for carrying out statistical averaging methods.

Again a beam splitter arrangement (with suitable reference detector(s)) may be located in the incident light beam path. This beam splitter arrangement may, for example, consist of a combination of a normal beam splitter (e.g., beam splitter cube) and a grating beam splitter or of a grating beam splitter operated in the zero-th or higher diffraction order (see also the section in-coupling angle scanning mode). One may determine a wavelength fluctuation from the shifts of the two light spots on the reference detector(s) in spite of possible simultaneously present beam stirring. One may also take this wavelength fluctuation into account on evaluating the shifting of the out-coupled light beams. The considerations with the grating in-coupler are the same as with the grating out-coupler as a result of the reciprocity theory of optics.

The in-coupling grating (or the in-coupling grating) of the waveguide structure consisting of at least one waveguide grating structure unit is (are) illuminated with a (one-dimensionally or two-dimensionally expanded) plane or (one-dimensionally or two-dimensionally expanded) slightly focussing wave(s) (light wedge strip or one(two) dimensional array of light wedges of equal or different focussing degrees).

Where appropriate, the slightly focussed incident light wave may be angularly set with the following device: The light beam is (almost) focussed with a cylinder lens onto a rotating mirror and from here is focussed or also only almost focussed with a second cylinder lens onto the in-coupling grating(s). By way of rotating the rotating mirror, the angle of incidence of the convergent light beam incident onto the waveguide grating structure also changes. The light beam may firstly (i.e., before it impinges the first cylinder lens) also be formed via a (simple or two-fold) (cylindrical) beam expander into a one-dimensional or two-dimensional light strip. The strip length is parallel to the rotational axis of the rotating mirror.

A one-dimensional light expansion is effected by way of a beam expander consisting of two cylinder lenses of differing focal width. A two-dimensional light expansion is effected either by way of a beam expander consisting of two spherical lenses of a differing focal width or in the case of light expansion into a light strip by way of a first beam expander consisting of two cylinder lenses of differing focal width and subsequently by way of a second beam expander consisting of two cylinder lenses of different focal width, wherein the cylinder axes of the second beam expander are perpendicular to the cylinder axes of the first beam expander.

The expanded light beam impinges a cylinder lens (cylinder axis is perpendicular to the plane of incidence) that produces the (slightly) focussed incident light beam (light wedge). The focus lies on or in the vicinity of the waveguide grating structure. Instead of a cylinder lens, one may use a one-dimensional or two-dimensional array of cylinder lenses (of the same or different focal width). A one-dimensional array of cylinder lenses (with a possibly light transparent or opaque intermediate distance) produces a one-dimensional array of light wedges that may be observed as a (grated) two-dimensional illumination of the waveguide grating structure. The light fields (light wedges) impinging on the waveguide grating structure illuminate the in-coupling gratings. A cylinder lens may also consist of several individual cylinder lenses (with a possibly light transparent or opaque intermediate distance). Thus, a two-dimensional array of cylinder lenses and, thus, a two-dimensional array of light wedges arise. Where appropriate, a further one-dimensional or two-dimensional array of cylinder lenses is present perpendicular to the cylinder axis of the first cylinder lens array. These cylinder lenses are to ensure that the light fields (light wedges) also are somewhat bundled perpendicular to the plane of incidence on the waveguide grating structure. The focus of these cylinder lenses may or may also not lie on the waveguide grating structure. In place of the crossed arrays of cylinder lenses one may also apply a one-dimensional or two-dimensional array of spherical lenses (with a possibly light transparent or opaque intermediate distance).

At least one light beam deflector may be located before and/or between and/or after the beam expanders. With this one may set the angle of incidence of the (one-dimensionally or two-dimensionally expanded) incident light beam. One may also apply two light beam deflectors connected behind one another, wherein one light beam deflector is responsible for the coarse adjustment and one light beam deflector for a fine adjustment. The fine adjustment, for example, is effected with electro-optical or acousto-optical deflectors. It is also possible with a light beam deflector to change the angle of incidence during the measurement. After the beam expanders there may also (but need not) be present the lens system that produces the light wedge (the light wedges).

If the incident light beam is led via a beam splitter and the two part beams subsequently are each deflected via a mirror onto the corresponding in-coupling gratings of the waveguide grating structure, then with one light beam deflector, which is located in front of the beam splitter, it may be achieved that the angle of incidence of the two part beams simultaneously becomes larger or smaller with regard to magnitude (see, e.g., FIGS. 5a-5b, wherein the x-components of the k-vectors (see FIG. 2) are to add).

If the light beam is linearly polarized, for example, at 45 degrees with respect to the plane of incidence, then TE waves as well as TM waves (preferably in the base mode) may be excited in the forwards and/or rearwards direction in the waveguide grating structure.

The light beam deflector (e.g., a EO or AO deflector) may also be applied in the scanning operation. With the scanning procedure the spots of the out-coupled light fields on the detector temporarily become bright and permit a location evaluation at least at this point in time.

One may excite one mode in the signal path (with chemo-functional signal layer) and one mode (of the same or different polarization) in the reference path lying next to this (with chemo-functional reference layer). With a different polarization, if the sensitivity is different, the differing sensitivity must be taken into account when referencing on the signal plane.

One may, however, also excite one mode in the forward and rearward direction or the TE-mode and the TM-mode in the forward and rearward direction, or the TE-mode and TM-mode in the forwards direction, or the TE-mode in the forward direction (rearward direction) and the TM-mode in the forward and rearward direction, or the TE-mode in the forward and rearward direction and the TM-mode in the forward direction (rearward direction) with a suitable choice of the waveguide grating structure unit. The chemo-functional sensor layer occupies at least partly the out-coupling grating of the waveguide grating structure unit or also the whole waveguide grating structure unit.

A lens system or a one-dimensional or two-dimensional array of lenses or lens systems is located between the waveguide grating structure and the position-sensitive detector (e.g., pixel array detector). The lenses may be spherical, cylindrical, or crossed cylindrical lenses.

With two crossed cylindrical lenses, for example, a cylinder lens (the cylinder axis is perpendicular to the plane of incidence) may be used for the angular measurement (i.e., the cylinder lens focuses almost onto the (array of) (position-sensitive) detector(s) (e.g., pixel array detectors) or an intermediate detector plane), while the other cylinder lens somewhat bundles the out-coupled light beam perpendicular to the plane of incidence.

Additionally, a (crossed) cylindrical and/or spherical, imaging lens optics may be located in front of the detector, which image an intermediate picture (on the intermediate detector plane) with lens optics (spherical and/or (crossed) cylindrical) onto a two-dimensional pixel array detector. If the spots in the intermediate picture shift, then they also shift on the pixel array detector.

The following lens system too may be located between the waveguide grating structure and the detector: A first cylinder lens (a first array of one-dimensionally or two-dimensionally arranged cylinder lenses) with cylinder axes perpendicular to the plane of incidence is operated in (almost) Fourier position. Where appropriate, a second cylinder lens crossed to the first cylinder lens (the cylinder axes of the first and second cylinder lens are perpendicular to one another) or a second array of one-dimensionally or two-dimensionally arranged cylinder lenses, which is crossed to the first array helps somewhat in bundling (or focussing) the out-coupled light beam(s) perpendicular to the plane of incidence. Even if the second array only consists of one large cylinder lens, one succeeds in bundling the light beams somewhat without them superimposing.

The (almost) Fourier plane may be considered as a fictive detector plane (intermediate detector plane). This fictive detector plane (intermediate detector plane) is imaged with two crossed cylinder lenses (systems) (of equal or differing focal width) (or with a spherical lens system or with a combination of spherical and cylindrical lens systems) onto a one-dimensional or two-dimensional array of (position-sensitive) detectors (e.g., pixel array detector). The image effected perpendicular to the plane of incidence is effected via that cylinder lens whose axis is parallel to the plane of incidence. The cylinder lens crossed to this images the (caused by a (bio)chemical reaction) shifting of the (fictive) light spot of the fictive detector plane (intermediate detector plane) onto the detector plane. This last cylinder lens may (but need not) have an enlargement ratio of one.

The compensation of perturbations may be effected with the concept of the signal path and reference path wherein, however, certain—subsequently mentioned—preconditions should be fulfilled.

For example, one may eliminate temperature fluctuations and non-specific binding (NSB) with the concept of the signal path and the reference path. A path consists of at least one grating or of at least one in-coupling grating and one out-coupling grating. The temperature fluctuations and the NSB should be equal or almost equal on the signal path and the reference path. The sensitivities of the signal path signal S (signal path) (effective change in the refractive index, change in the in-coupling angle (with the incident angle scanning mode and/or the out-coupling angle scanning mode), wavelength change (with the wavelength scanning mode), intensity change, change in the intensity of the fluorescence (luminescence, electroluminescence, chemoluminescence, phosphorescence signal) and of the corresponding reference path signal S(reference path) should be equal or almost equal. For this it is necessary (or, however, at least advantageous) if the chemo-functional signal layer (on the signal path) and the chemo-functional reference layer (in the reference path) belong to the same class of chemo-functional layers. The following classes are distinguished: (1) binding or reaction take place at the surface of the chemo-functional layer; (2) binding or reaction take place in the volume of the chemo-functional layer; (3) binding or reaction take place in the volume as well as on the surface of the chemo-functional layer.

The perturbation signal $\Delta S$ (e.g., effective change in the refractive index $\Delta N$) in the first order is the sensitivity $\delta S/\delta X$ (e.g. $\delta N/\delta X$) allocated to the perturbation effect $\Delta X$ and multiplied by the perturbation effect $\Delta X$. With the same sensitivity and the same perturbation effect on the signal path and reference path there is valid S(signal path)+$\Delta$S(signal path)−S(reference path)−$\Delta$S(reference path)=S(signal path)−S(reference path)=referenced sensor signal. The perturbation effect is referenced away. The signal S is mostly detected itself as a signal change $\Delta S$. Two important perturbations are the temperature fluctuation and the non-specific binding (NSB). There are, however, also other perturbations such as wavelength fluctuation, beam stirring, diffusion of molecules (atoms, ions) into the waveguide structure, swelling of the chemo-functional layers, thermo-optical and photochemical effects, etc.

With a temperature fluctuation $\Delta T$ (=perturbation effect) on both paths, the relevant sensitivity is $\delta N/\delta T=(\delta N/\delta n_c)(\delta n_c/\delta T)$, wherein $n_c$ is the refractive index of the cover medium C. The other amounts—such as, for example, $(\delta N/\delta n_F)(\delta n_F/\delta T)$, wherein $n_F$ is the refractive index of the waveguiding film F—are omitted, since these (more or less) cancel on referencing. The referencing of the perturbation signal is $\Delta N(S)-\Delta N(R)=((\delta N/\delta n_c)(S)(\delta n_c/\delta T)(S)-(\delta N/\delta n_c)(R)(\delta n_c/\delta T)(R))\Delta T$, wherein S indicates the signal path and R the reference path. The same sensitivity $\delta N/\delta n_c$ and the same temperature coefficient $\delta n_c/\delta T$ on both paths allow the perturbation signal to cancel when referencing. If, for example, with the binding onto the surface of a thin (e.g., monomolecular, e.g., approx. 10 nm thick) chemo-functional signal layer, the reference path is covered with a shielding (solid state) layer (e.g., of $SiO_2$) (the shielding prevents the interaction of the evanescent wave with the sample), then the referencing does not function since the temperature coefficient $\delta n_c/\delta T$ on the signal path (=temperature coefficient of the liquid sample) and the temperature coefficient $\delta n_c/\delta T$ on the reference path (=temperature coefficient of the solid body)

are different. Liquids and solid bodies have temperature coefficients that differ by about one order of magnitude.

Figure 9:
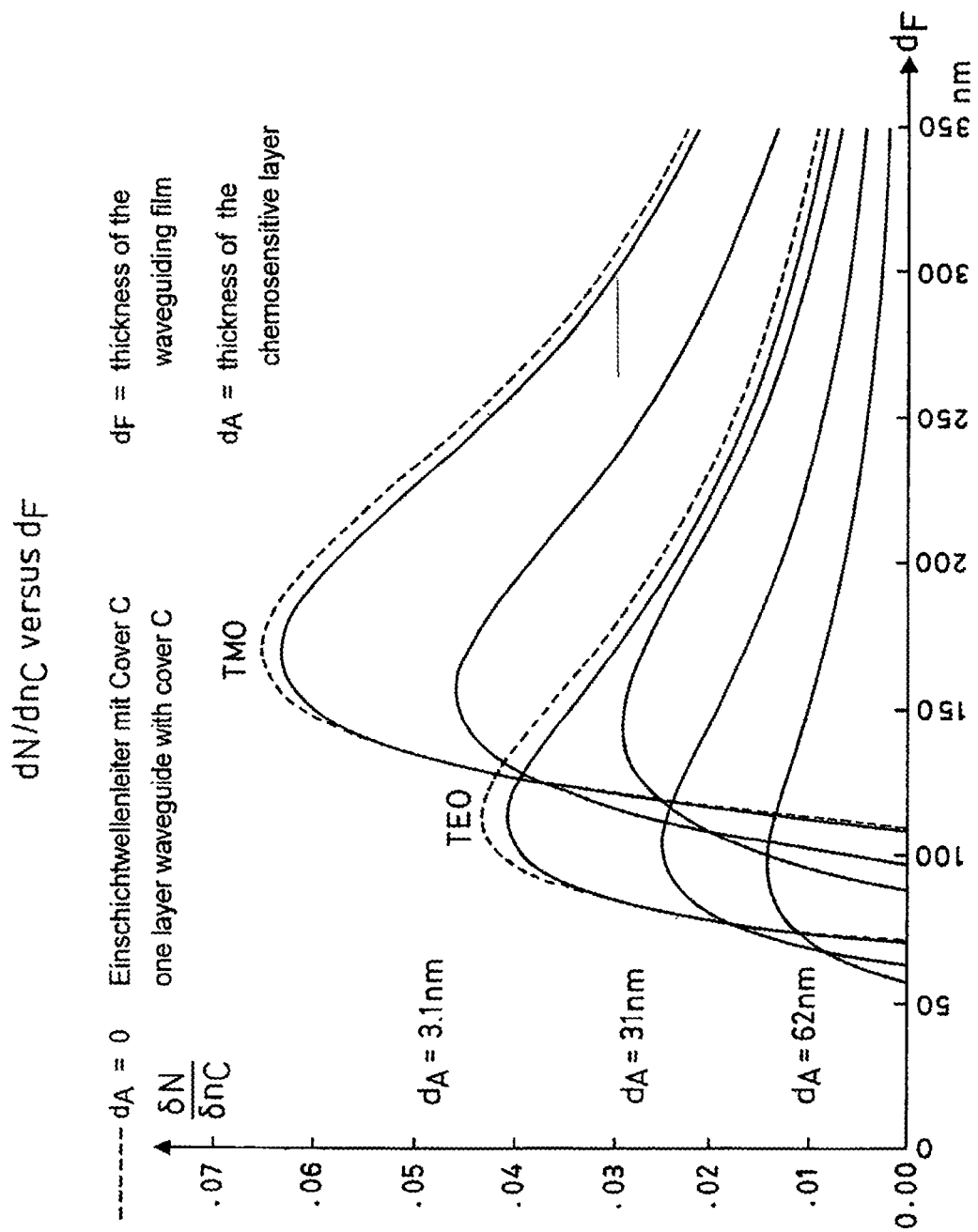
FIG. 9 shows the sensitivity dN/dnC of a waveguide with respect to the refractive index change dnC of the cover medium C as a function of the thickness dF of the wave-guiding film F.

FIG. 9 shows the sensitivity dN/dnC of a waveguide with respect to the change in refractive index dnC of the cover medium C as a function of the thickness dF of the chemo-sensitive layer F. The sensitivity curves depend on the thickness layer dA of the chemo-sensitive layer. The larger the thickness layer dA the smaller the sensitivity becomes. TE0 indicates the transverse electric mode with mode number 0 and TM0 the transverse magnetic mode with mode number 0.

So that the sensitivities with respect to a temperature fluctuation on both paths are roughly equal in the case of surface area binding, the layer thickness of the chemo-functional signal layer and that of the chemo-functional reference layer must be roughly equal. If, however, the evanescent wave in both paths runs completely in the respective chemo-functional layer, then the layer thicknesses of the chemo-functional layers play no part.

Figure 10:
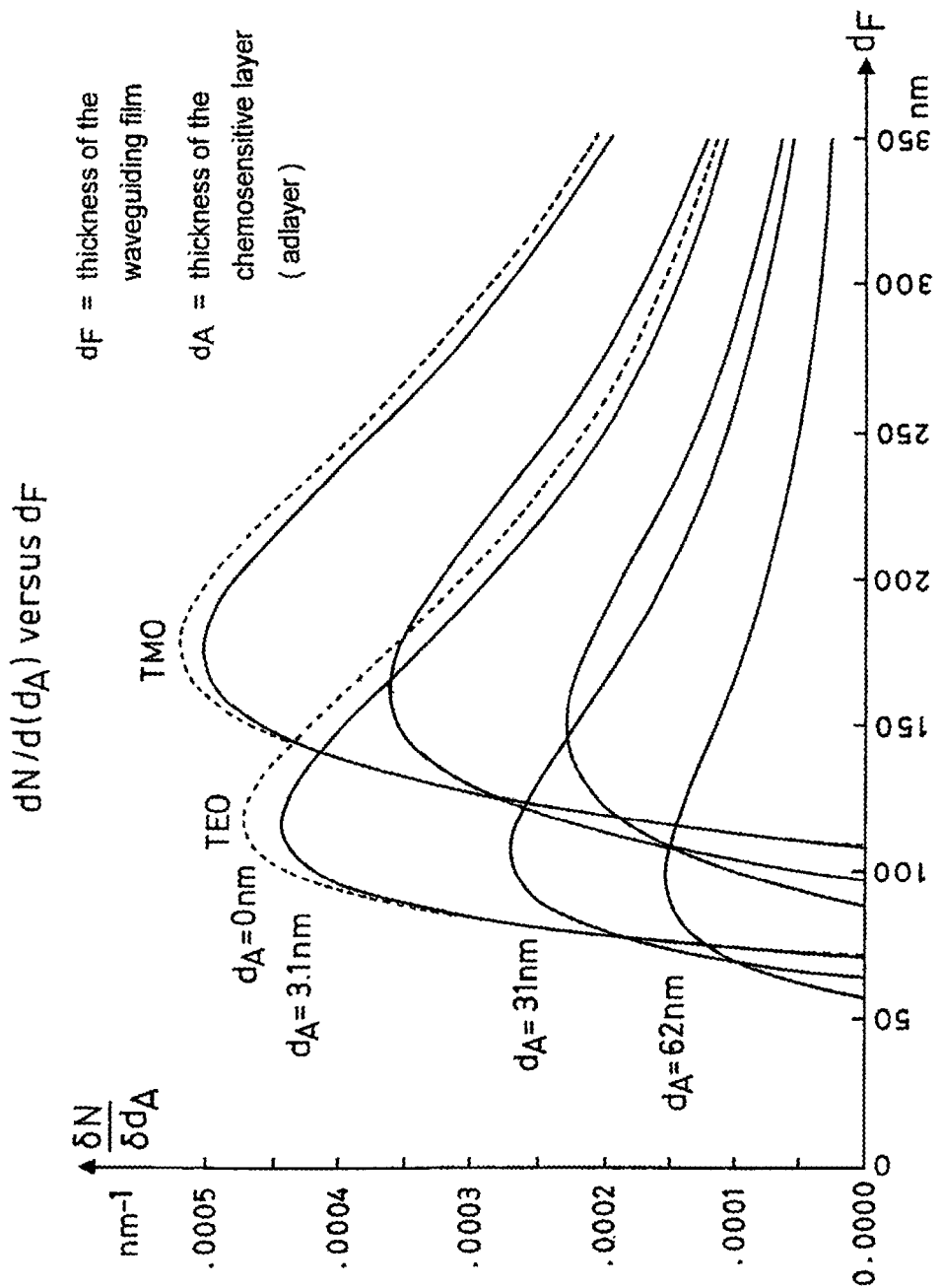
FIG. 10 shows the sensitivity dN/d(dA) of a waveguide with respect to a layer thickness change d(dA) of the chemo-sensitive layer A (A=adlayer) as a function of the thickness dF of the waveguiding film F; and, FIG. 11 shows a measurement construction in a schematic manner, with which the detection system is not in the reflected beam path

FIG. 10 shows the sensitivity dN/d(dA) of a waveguide with respect to a layer thickness change d(dA) of the chemo-sensitive layer A as a function of the thickness dF of the waveguiding film F. The sensitivity curves depend on the layer thickness dA of the chemo-sensitive layer (A=adlayer). The larger the layer thickness dA, the smaller does the sensitivity become. TE0 indicates the transverse electric mode with mode number 0 and TM0 the transverse magnetic mode with mode number 0. Equal non-specific binding (NSB) (equal mass coverage) onto the surface of a thicker chemo-sensitive layer thus compared to equal NSB (equal mass coverage) onto a thinner chemo-sensitive layer leads to a smaller effective change in refractive index, since the sensor signal (e.g., change of the effective refractive index) in the first order (linear case) is the product of sensitivity and perturbation effect.

If a binding (or the NSB) onto the surface with the chemo-functional signal layer and with the chemo-functional reference layer takes place with roughly equal intensity (with the same coverage density) (mass coverage) and if both chemo-functional layers are equally thick or almost equally thick, then the sensitivities (see FIG. 10) of both paths are equal or almost equal and thus also the perturbation signals. With the referencing of the signal (e.g., the effective refractive index (change)), in-coupling angle (change), wavelength(s) change, out-coupling angle (change), etc.) as a result, the perturbation signals of the two paths are subtracted away.

In order generally to be able to measure bindings on the surface, the thickness dA of the chemo-functional layer may not be too large (see FIG. 10). This is because the sensitivity dramatically reduces with thicker chemo-functional layers. The thickness of the chemo-functional layers should be smaller than the wavelength, or lie below 100 nm. Preferably, one uses monomolecular layers or self-assembled monolayers (where appropriate with (bio)chemical structures building up on this).

It is also advantageous to illuminate the signal path and the reference path simultaneously and with roughly the same intensity. By way of this, roughly on both paths the same photo-chemical and thermo-optical perturbations are effected and may therefore be referenced or subtracted away. Thermo-optical effects in combination with waveguide grating structures are described in Thin Solid Films 126 (1985), 197-203. In order to keep the photometric and thermo-optic perturbations low it is basically possible (a) to operate with a low light intensity and/or (b) to operate in pulse operation. On the other hand, of course, the light intensity must be sufficiently high in order to produce a measurement signal, which lies clearly above the background noise.

If at a sensor location (waveguide grating structure with chemo-sensitive layer) the modes TE and TM in the forward and rearward direction (mode number preferably equal to zero) are measured with a scanning mode, then likewise with evaluation methods as they are described in WO 99/13320—but preferably using waveguide grating structures with beam separation—one may generate sensor signals with a reduced temperature dependency. The sensor signal, for example, may be the layer thickness of the waveguiding film (in the three-layer model) or the layer thickness of the additional layer (with or without (bio)chemo-sensitive layer), and may be computed from a linear equation system with the sensor signal and the temperature fluctuation $\Delta T$ as the unknown variables. The temperature coefficient $\delta N/(\ )/\delta T$ (=derivative of the effective refractive index N according to the temperature T with respect to a mode type (( )=TE or ( )=TM)) is more often than not used as an input variable.

The considerations with regard to the beam guiding of the incident light beam (of the incident light beams), to mode excitation, to beam expansion, and to the light beam deflectors are also valid for all scanning modes—thus also for the wavelength scanning mode or incident angle scanning mode—, wherein with the wavelength scanning mode or the incident angle scanning mode (preferably) one does not use incident light wedges. The mode excitation, however, is effected with the scanning method. The detection mechanism in combination with the corresponding scanning mechanism is described with the respective scanning mode. The lens system located between the waveguide grating structure and the detector may be operated in the imaging position (or almost imaging position) and/or Fourier position (or almost Fourier position).

The waveguide grating structures (with or without referencing) as they are, for example, described in FIGS. 2*a*, 2*b*, and 2*c*, may be read out also in the wavelength scanning mode or the incident angle scanning mode (in-coupling grating and out-coupling grating for one mode taken together may also form only one grating). During the scanning procedure mode excitation occurs with all four gratings. The incident light beams are preferably polarized at 45 degrees with respect to the plane of incidence in order to be able to excite the TE-waves as well as TM-waves. Either the light attenuation occurring in a resonance-like manner on mode excitation and/or the (in a displaced manner appearing) light intensivation and/or the maximal (absolute) increase of the light distribution between the light attenuation region and the light intensivation region and/or the light center of intensity shifting of the light distribution is measured during the scan of the pixel array detector in a locally resolved manner. If the gratings are superimposed, one loses the local resolution. Therefore, the grating periods must be selected such that during a scanning procedure the resonance characteristics occur temporally after one another. The waveguide may (need not) be absorbing (where appropriate in a laterally dependent manner).

The chemo-sensitive layer may, for example, be deposited with a spotter. With scatter light measurements and/or fluorescence measurements, several (various) chemo-sensitive layers arranged array-like in a one(two)-dimensional manner may also be located between two gratings or on an extended grating (one-dimensional arrangement parallel or perpendicular to the grating lines or two-dimensional arrangement). Scatter light, luminescence light, fluorescence light, phosphorescence light may be supplied being guided with a fiber bundle (with or without deposited lens array) or with a lens system or with a lens array, a detector, or detector array.

A one-dimensional array of (various) chemo-functional layers between two gratings (of the same or differing grating periods) may also be applied with monochromatic interferometric direct measurements (marking-free measurements) (compare with R. G Heidemann et al., Development of an Optical Waveguide Interferometric Immunosensor, Proceedings Eurosensor 4, Karlsruhe 1990). A reference path (with or without equally large chemo-functional reference layers in the mode direction) is allocated to each signal layer of a one-dimensional signal layer array running parallel to the grating lines, or a reference path (with or without equally large chemo-functional reference layers in the mode direction) is allocated to several (or all) one-dimensionally arranged signal layers. Passivation material preventing NSB, where appropriate, covers the sensor chip outside the chemo-functional layers. The in-coupling grating may be grated consisting of several individual gratings (with an intermediate distance), wherein the individual gratings in each case supply the light for a signal layer (or reference layer). With a continuous grating, the grating may be covered with a cover layer in the region of the intermediate distance in order to permit light in-coupling only outside the cover layer. The in-coupling grating (the individual gratings) may be illuminated with a light strip or light strip wedge. The out-coupling grating, where appropriate, may be grated consisting of several individual gratings (with or without intermediate distance). Grating periods, grating focussing, grating orientation of the individual gratings and, where appropriate, the lens array located between the out-coupling grating and detector array (pixel array detector) are designed such that the respective Mach Zehnder arms interfere on the one(two)-dimensional detector array (e.g., pixel array detector). The plane of the detector array may also be an intermediate plane, which then is imaged onto a detector plane in a spherical, cylindrical or crossed cylindrical (with different focal widths) manner. The described waveguide grating structure may be extended in a one(two)-dimensional array-like manner. The incident light is several light strips or light strip wedges or a expanded light beam. The manufacture of the incident light is described further above. One may, however, operate with only one two-dimensional detector array (e.g., pixel array detector).

The grating may also be modulated, wherein a grating region with modulation depth=0 may indeed occur in a locally resolved manner and means that no grating lines are present. The one(two)-dimensional array of chemo-sensitive layers may, for example, lie in that region which has no grating lines. The grating periods also need not be constant.

If a beam splitter is located in the beam path of the radiated light wave(s), then simultaneously in a (first) beam path (with wavelength filter in order to block out light of the excitation wavelength) fluorescence (luminescence, phosphorescence) light may be measured and, in the other beam path, simultaneously or not simultaneously one may measure a direct binding assay. In the other (second) beam path there may also be located a wavelength filter that blocks out the fluorescence (luminescence, phosphorescence) light. The lens system(s) may be located before and/or after the beam splitter. For example, a lens (lens system) located between the sensor chip and the beam splitter may act as an imaging lens for the first beam path (path for the marking measurement) and for the second beam path (path for marking-free measurement) act as (almost) Fourier lens(system). The lens (the lens system) may, however, also act in an imaging manner for both beam paths (e.g., with the incident angle scanning mode or wavelength scanning mode with combined fluorescence (luminescence, phosphorescence) measurement). The measurements on the marking-free path may also serve as referencing (e.g., referencing the intensity of the excitation wave with fluorescence (luminescence, phosphorescence) measurements). The referencing also functions if a marking-free measurement is carried out parallel to this. The molecular weight of the label (or labels) must be taken into account in certain assay formats.

With an incident angle scan (or wavelength scan) the wave radiated (out-coupled) in the second beam path (path for marking-free measurement) runs through a resonance curve. The fluorescence (luminescence, phosphorescence) light radiated in the first beam path (path for the marking measurement) likewise runs through a resonance curve, which may now be referenced with the resonance curve of the first beam path. The accuracy is increased by way of the fact that a resonance curve is employed for referencing.

However, one may also operate with a fixed angle of incidence and the lens (the lens system) may act in an imaging manner for both beam paths. With fluorescence (luminescence, phosphorescence) light measurements, the intensity or intensity distribution measured with the detector (detector array) located in the second beam path serves as a reference (reference intensity distribution) for the fluorescence (luminescence, phosphorescence) light intensity (distribution) measured with the detector (detector array) located in the first beam path. In this case reference preferably means a formation of a ratio (marking intensity/excitation intensity). The excitation intensity is advantageously measured via out-coupled (radiated) light waves.

With the use of a fiber bundle one may, however, also imagine that the fiber bundle and lenses (lens system(s)) are exchangeable or displaceable. With the fiber bundle, for example, one carries out a marking measurement (fluorescence, luminescence, phosphorescence) and, with the lens (with the lens system(s)), one carries out an incident angle scanning mode. The fiber bundle (with or without attached lens system or lens array) preferably accommodates the light (fluorescence, luminescence, scatter light) from the non-modulated part of the waveguide grating structure. The wavelength filter is located between the fiber bundle and the detector, or between the sensor chip and fiber bundle, or between two fiber bundle parts. The end of the fiber bundle, where appropriate, may be imaged with a lens (with a lens system or lens (system) array) onto the detector (detector array). The intensity of the excitation wave is referenced in that a beam splitter is set up in the incident beam path and the intensity of the light reflected by the beam splitter is detected with a detector (detector array). However, also (possibly additionally) the intensity of the excitation light reflected or diffracted (before and/or after the chemo-sensitive layer(s) and/or below the chemo-sensitive layers) by the sensor chip may be measured with a detector (individual detector, one(two)-dimensional detector array) (e.g., pixel array detector) with or without prearranged spherical or cylindrical imaging optics and with or without a wavelength filter, for referencing.

It is also possible to provide a larger (stronger) modulated waveguide grating (with or without damped (absorbing) waveguide) with a one-dimensional or two-dimensional array of chemo-sensitive layers. The resonance in-coupling curve is relatively wide on account of the increased modulation. The incident light beam exciting the mode may be fixed during measurement or may also be operated in the incident angle scanning mode. The wavelength is selected such that fluorescence (luminescence) excitation is possible. The surface of the sensor chip is imaged with a lens (a lens system) on an array of detectors or onto the end surface of a fiber bundle. The light distribution of the other end of the fiber bundle is then led with or without a lens (lens system, lens array) to an array of detectors. A wavelength filter that only lets through emission light is again located between the sensor surface and detector. A beam splitter may again be located in the radiated light, which permits a referencing of the emission light with respect to the radiated and/or out-coupled excitation light (excitation scatter light) via the second beam path (see further above) where appropriate with a wavelength filter blocking emission light.

With the incident angle scan (or wavelength scan) the fluorescence of each sensor location runs through a maximum since the exciting evanescent wave likewise runs through a maximum with respect to intensity. The reflected or diffracted light wave may be incident onto a one(two)-dimensional detector array (e.g., pixel array detector) via a spherical or cylindrical beam compressor or imaging optics with or without a beam splitter with or without a wavelength filter, and serves as a reference.

The intrinsic fluorescence of a waveguide grating structure on a plastic substrate may be kept small in that an inorganic layer is located between the plastic substrate and the waveguiding film, whose refractive index is deeper than that of the waveguiding film and whose thickness is preferably greater than the penetration depth of the exciting guided light wave. The grating structure in this case may, for example, be photolithographically deposited into the inorganic layer or into the inorganic waveguiding film.

Other measuring technology is based on the measurement of emission light (fluorescence, luminescence, phosphorescence light) on waveguide (grating) structures in combination with a direct measurement. With this, a layer of the waveguide structure (consisting of one or more layers) and/or a layer between the waveguiding film and the substrate and/or a layer between the waveguiding film and cover (or (bio)chemofunctional layer) and/or a layer on the underside of the substrate and/or the substrate itself is light-emitting (fluorescence, luminescence, phosphorescence light) on excitation with light (with a wide and/or narrow excitation spectrum). This layer may, for example, be a polymer layer (or a solid-body-like layer or a glass-like layer) with a (high) intrinsic fluorescence or with embedded emission light molecules (fluorescence, luminescence, phosphorescence molecules). The emission light wavelength is different to the excitation wavelength. The method systematics are based on the incident angle scanning mode or on a wavelength scanning mode (with a tunable light source), wherein in the beam path between the sensor chip and the detector there is located a wavelength filter (blocking the excitation light, transparent to the emission light). A beam splitter may also be located between the sensor chip and the detector, wherein then the wavelength filter is preferably in the beam path between the beam splitter and detector. The excitation light may, for example, be incident onto the sensor chip ((bio)chemo-functional waveguide grating structure) via the beam splitter. The excitation light may also be incident obliquely from the substrate side or obliquely from the cover side onto the sensor chip, wherein the beam splitter may or may not be present. The emission light may also (preferably) be measured in a direction that does not correspond to the reflection direction of the excitation light beam. The incident light beam on fulfilling the in-coupling equation produces a guided light wave, but may also excite emission light that by way of the led mode is directly or indirectly (resonance-like) intensified and/or shifted with respect to center of intensity. The (radiated and/or out-coupled) emission light of the emission layer is imaged onto the detector. The out-coupled light of the excitation wave may or may not be incident onto the imaging lens. The measuring systematics represents a combination of direct measurement with fluorescence (luminescence, phosphorescence) measurement. Since with the wavelength scanning mode the (excitation) wavelength is shifted, the excitation spectrum must be sufficiently broad. Light-emitting mode-beating patterns (between the TE mode and TM mode) and light-emitting interferometric patterns with and without (uni-diffractive or multi-diffractive) gratings with scanning operation (incident angle scanning mode or wavelength scanning mode) or without scanning operation (excitation of the modes TE and/or TM with plane or slightly focussed waves) may be measured with the application of polarizer (e.g., 45° polarizer) located between the sensor chip and the detector in the case of interference of TE-light and TM-light, and with the application of the mentioned wavelength filter at the point in time of mode excitation, wherein the modes of the excitation wavelength are produced via grating in-coupling. A binding reaction (or mass accumulation) or chemical reaction (change of the complex refractive index) on the (bio)chemofunctional layer, which is located on and/or next to the grating, changes the periods of the interference pattern.

Basically, for all measuring techniques all detectors (detector array, pixel array detectors) may also be cooled detectors. Cooled detectors are particularly applied with signals that are weak in light. The cooling may, for example, be effected with Peltier elements. The quantity of detectors is indicated as the detector device.

Basically, one may also apply absorbing or greatly absorbing waveguides or waveguiding films or waveguiding materials (with or without locally dependent light-absorbing structuring). The waveguiding film may, for example, be of black glass or be coated with an absorbing material (metal, chromium, gold, silver, aluminum, tin, zinc, titanium, dye, silicon, colored glass, colored polymer, colored lacquer, polymer metal compounds, etc). The absorbing material may, however, also be present as a thin layer. This thin layer may be located at the interface substrate/film, or film/chemo-sensitive layer, or film/cover, or within the waveguide structure (in the case of a multi-layer system). If the (bio)chemo-sensitive layer sees the oxide surface, one may use simple methods for immobilisation. The waveguiding film (or at least a layer of the waveguide structure) should comprise a large real component of the complex refractive index. The waveguiding film may, for example, consist of tantalum oxide ($Ta_2O_5$), titanium oxide ($TiO_2$), zirconium oxide ($ZrO_2$), hafnium oxide ($HfO_2$), niobium oxide, oxynitride, $Si_3N_4$. The black glass may, for example, be deposited with sputtering technology. The substrate may be glass or plastic.

An absorbing waveguide has a greatly shortened coupling length. An absorbing waveguide represents a dissipative system, i.e. the energy of the guided light wave is given off to the waveguide. With a waveguide grating structure then, in the case of mode excitation, this energy is lacking in the directly radiated diffraction orders.

If the waveguide is not absorbing, one may deposit a layer (e.g., colored polymer layer, colored lacquer layer, colored glass layer, metal layer, semiconductor layer, polymer-metal compounds, etc.) between the gratings, this layer then acting as a mode stopper. The molecules of this layer may (need not) penetrate into the waveguiding film. The deposition of this layer stopping the mode may, for example, be effected with a spotter. This layer stopping the mode may also be present in the form of a circular ring and where appropriate enclose a chemo-sensitive layer.

Absorbing waveguides, out-coupling gratings, and also stop gratings, stop tapers, stop slots (with or without interruption of the waveguiding film) help in the reduction of crosstalk between two sensor locations.

Non-absorbing waveguides with a greatly modulated grating also display a short coupling length. The energy of the guided light wave is, however, heated in the waveguide.

Figure 11:
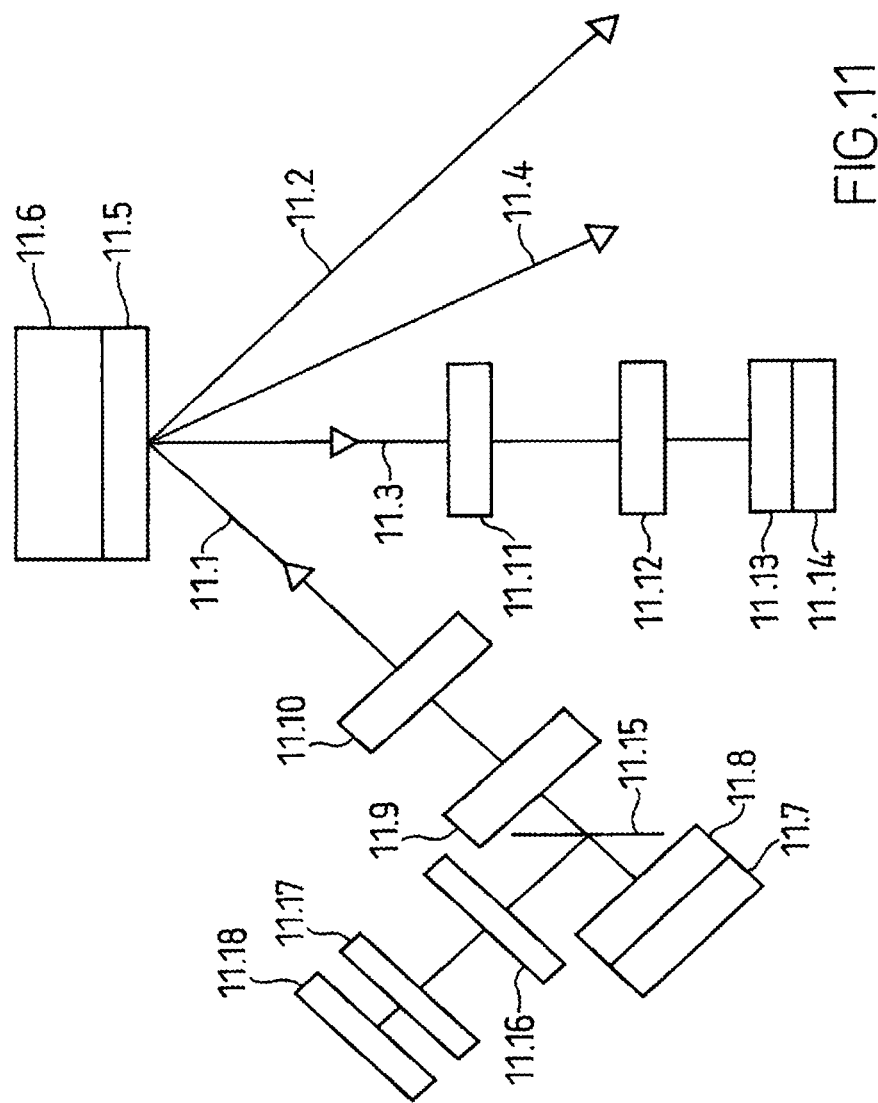

FIG. 11 shows a possible measurement arrangement for reading out in parallel a one-dimensional and/or two-dimensional array of (chemo-functional) waveguide grating structure units in a schematic manner.

The incident light beam 11.1 is present as an expanded light beam or as a light beam bundle. The reflected beam 11.2 does not run into the detection device 11.11 to 11.14. The light field 11.3 may be a diffraction order of the waveguide grating structure, but may, however, be only one scatter light field (or fluorescence light field). A further diffraction field 11.4 (if present) does not enter the detection device 11.11 to 11.14.

The waveguide grating structure 11.5 consisting of at least one waveguide grating structure unit or a sensor location, where appropriate, is connected to a liquid holding device 11.6 consisting of a well or a flow-through cuvette or a capillary cuvette of an array of wells and/or flow-through cuvettes and/or capillary cuvettes.

The light source 11.7 produces the light and, where appropriate, is already equipped with first optics (e.g., collimation optics).

The lens system (or array of lens systems) 11.10 produces an expanded light beam or a light beam bundle (=bundle of (expanded and/or (weakly) focussing) light beams).

The lens system (or array of lens systems) 11.11 deflects the radiated or out-coupled light fields in a locally resolved manner onto the detector 11.13. The lens system (or array of lens systems) 11.11 may operate in an imaging manner (or an almost imaging manner), acting as a Fourier lens(es) (or as an almost Fourier lens(es)) or in a focussing (or slightly focussing) manner or in a light-collecting (or slightly light-collecting) manner.

The detector 11.13 consists of an array of detectors, which in a locally resolved manner measures the light intensities. The detector 11.13 may also be a pixel array detector, which may be construed as a special array of detectors. The detector may, however, also consist of an array of position-sensitive detectors.

The scanning device 11.8 (wavelength scanning device in the light field which beams into the waveguide grating structure, wavelength shifter), 11.9 (angle scanning device, light beam deflector or light beam deflector system for the coarse and fine adjustment), 11.12 (wavelength scanning device in the light field radiated from the waveguide grating structure), 11.14 (read-out device for reading out the light field measured by the detector 11.13 or the measured intensity distribution) relate to different measurement modes, wherein the read-out device 11.14 of the detector is always present.

The wavelength scanning device 11.8, where appropriate, including the wavelength shifter for the coarse adjustment relates to the wavelength scanning mode (type I). The light beam deflector 11.9 need not be present, but may, however, be used for the coarse adjustment (fixing a favourable scanning interval). The wavelength scanning device 11.12 is not present.

The wavelength scanning device 11.12 relates to the wavelength scanning mode (type II). The light beam deflector 11.9 need not be present but, however, where appropriate may be used for the coarse adjustment (fixing a favourable scanning interval). The wavelength scanning device 11.8 is not present (or is present in the form of a broad-band filter for fixing a maximal measurement interval).

The angle scanning means 11.9 relates to the incident angle scanning mode. With this the wavelength scanning device 11.12 is not present. The wavelength scanning device 11.8 need not be present but may, however, where appropriate be used as a wavelength shifter for the coarse adjustment (fixing a favorable scanning interval) (Take note: with wavelength changes the sensitivities of the waveguide grating structure also change (see and compare Thin Solid Films 126 (1985), 205-211) and must (may) be taken into account on evaluation. The coarse adjustment may, however, also be carried out with a second light beam deflector.

In any case, with the out-coupling angle scanning mode one also requires the read-out device 11.14. The light beam deflector 11.9 and/or wavelength shifter 11.8 may be used for coarse adjustment. With the wavelength shifter, where appropriate, the sensitivities (see and compare Thin Solid Films 126 (1985), 205-211) must be recorrected.

With fluorescence (luminescence) measurements 11.12 may also represent only one wavelength filter (with or without scanning device).

A liquid holder or sample accommodating device or a cuvette (well cuvette, through-flow cuvette, capillary cuvette) or an array of liquid holders and/or sample accommodating devices and/or cuvettes and/or combinations thereof may be located above the waveguide grating structure unit(s). The liquid holders, sample accommodating devices, and cuvettes are preferably dark (black). The adhesing material between the sensor chip and the cuvette (sample accommodating device, liquid holder) is preferably also dark or black. Dark (black) materials reduce the scatter light and, thus, the crosstalk.

A special liquid holder (sample holder) may represent a liquid droplet (sample droplet) hanging on a needle (injection needle) or pipette tip, which contacts the sensor location(s) without the needle (injection needle) or pipette tip contacting the sensor chip. This situation may, for example, be controlled with a distance sensor. A movement of the fluid (sample) may be achieved by way of a slight ejection and suctioning of the fluid (sample). The movement of the liquid (or sample) helps in suppressing non-specific binding. An array of injection needles or pipette tips brings the samples or the sample droplets onto the array of (chemo-sensitive) waveguide structure units or sensor locations. The array of sample feed devices (e.g., injection needles or pipette tips) may be connected to the sensor chip via samples during the measurement. The array of sample supply devices and the sensor chip, where appropriate, may have (separate) tempering devices (with or without the application of Peltier elements) with associated temperature controls. The array of sample supply devices (e.g., injection needles or pipette tips) may, however, be completely removed after depositing the samples or sample droplets onto the sensor chip. The contact between the sensor chip and the sample supply device via the samples thus only exists temporarily. The sample droplets adhere by way of the surface tensions (surface forces), which so to speak represent intrinsic sample holders. The wells may be incorporated into the sensor chip and only have slight depths. However, no wells may be present.

A stirrer may be added into a well cuvette or a pipette tip, or injection needle introduced. The fluid may be kept in motion with the stirrer. The fluid (or sample) may be continuously supplied and suctioned via a pipette tip or injection needle. The suctioning may also be effected via a second pipette tip or injection needle, by which means a through-flow arises. With this there also arises a movement of the liquid (or sample). The movement of the liquid (or sample) helps in minimizing non-specific binding (NSB). With the through-flow cuvette one automatically has a movement of the fluid (or sample) with the through-flow. With the capillary cuvette the movement of the liquid (or sample) arises on account of the capillary effect. If the capillary is filled then without further, the movement of the liquid (or sample) also comes to a standstill.

The liquid holder (sample holder) or sample accommodating device or cuvette may be designed in various manners. The sample (or fluid) located in the device may, for example, contact only one chemo-functional signal layer where appropriate including the chemo-functional reference layer, i.e. a device (through-flow cell, open cuvette, well, capillary cuvette, etc.) is located over each chemo-sensitive signal layer, where appropriate, including a chemo-functional reference layer. However, a separate device may be located over the chemo-functional reference layer.

However, also several (or even all) chemo-sensitive layers may be located below a device. In this case one and the same sample contacts several (or even all) chemo-sensitive layers. The device with the several chemo-sensitive layers may be extended in a matrix-like or circular ring-like manner and, thus, form an (overriding) array. The matrix-like extension may, for example, be the form of a well plate (with, e.g., 24, 48, 96, 384, 1536 wells, etc.) or of a microarray. A (matrix-like) arrangement of chemo-sensitive layers is then located below each device (e.g., well). However, where appropriate also only one chemo-sensitive layer may be located below each device. If the sample contacts the chemo-functional signal layer and the chemo-functional reference layer in the same device or sample holder, then the temperature equality on both paths is very well ensured.

The reference path (with or without chemo-functional reference layer) may also be covered only with water or a buffer solution (advantageously the buffer solution of the sample). Advantageously—in the case of surface interaction—the thickness of the chemo-functional reference layer is equal or almost equal to that of the chemo-functional signal layer in order to ensure the equality of the sensitivity (for example, temperature sensitivity). Since the buffer solution contains no biomolecules, no NSB of the biomolecules may occur in the reference path. The chemo-functional signal layer and the chemo-functional reference layer may (need not) be identical here. In this case the signal path and the reference path have a separate liquid accommodating device (well, through-flow cuvette, capillary cuvette, liquid holder (sample holder), etc.).

The through-flow cells may be provided with a supply tubing and removal tubing. The through-flow cuvette (or capillary cuvette) may, however, be provided with at least one membrane through which the needle of a liquid handling system may pierce and supply (or remove) the sample. However, one (two) pipette tip(s) or needle(s) may be moved to the through-flow cell (or capillary cuvette) via a sealing device and contact this on the supply side and/or removal side in a fluid-tight manner. The movement of the fluid (or sample) is effected by knocking the fluid (or sample) from the supply side or by suctioning the fluid (or sample) from the removal side.

The wells or through-flow cuvettes or capillary cuvettes may be attached as separate sample cells (or sample cell plate) onto the waveguide grating structure consisting of one or more waveguide grating structure units (sensor locations). It is, however, also possible to provide the substrate with recesses such that these recesses already assume the function of the wells or of the through-flow cuvettes or of the capillary cuvettes. In the latter two cases the waveguide grating structure must be covered over with a cover plate provided with bores. In the first case the waveguide grating structure may be covered over with a cover plate (without bores) in order, for example, to prevent evaporation. The bores serve the supply or removal of the liquid (or sample) and or the bleeding.

In order to further increase the sensitivity per sample volume unit, it is also advantageous to let the sample run over a sensor location consisting of at least one sensing pad of a waveguide grating structure unit with possible referencing. This may, for example, be achieved in that the sample in the case of a through-flow cuvette is alternately moved (pumped) forward and rearward. Another possibility envisages the through-flow cuvette being part of a sample loop. In the sample loop it has a liquid movement device (e.g., pump), which has the effect that the sample quantity enclosed in the loop is moved over the sensor location in a circular manner in one direction and/or alternately forward and rearward. The sample loop is preferably filled via a valve (system) and closed, wherein preferably one applies valves, which have as low as possible dead volume or even with a dead volume=0. The sample loop may at least partly consist of tubings and/or also be part of a lab-on-chip system. The advantage of a lab-on-chip system is the fact that valves, movement device (e.g., pump), and liquid channel are integrated on a chip (lab-on-chip). The sensor location may be located on a separate sensor chip, which may be brought into contact with the lab-on-chip or may be integrated on the lab-on-chip. In the latter case, for example, at least one sensing pad (with or without referencing) is integrated into the liquid channel wall. The liquid channel wall then at one or several locations in parallel (on opposite liquid walls) or in series comprises a waveguide grating structure with preferably different (bio) chemo-functional signal layers (and where appropriate with (bio)chemo-functional reference layers). The sensor location and the device for fluid movement (e.g., pump) may be arranged in series in the liquid channel or may also be present in parallel (i.e., lie opposite). Several liquid channels may also be present in parallel. The sensor locations of the liquid channels may be read out parallel or in series. By way of a suitable valve control design one may activate the liquid channels parallel with the same sample or parallel with various samples. The liquid channels may also be activated individually.

The sensitivisation of the sensor location (deposition of the (bio)chemo-functional layer), where appropriate, may also be effected with suitable valves via a second liquid channel system. By way of a suitable switching of the valves, the sensor location may thus, on the one hand, be a component of the first liquid channel system and, on the other hand, be a component of the second (or even third, fourth, etc.) liquid channel system. The immobilization of the (bio)chemo-sensitive layer may, for example, be effected via the second channel system.

A special waveguide grating structure consisting of one (two) in-coupling gratings and one (two) out-coupling gratings with a (bio)chemo-functional signal layer lying therebetween (and where appropriate a (bio) chemo-functional reference layer lying next to this) may also be operated as a Mach Zehnder interferometer, wherein a Mach Zehnder arm leads over the (bio)chemo-functional signal layer and the other Mach Zehnder arm over the (bio)chemo-functional reference layer (see R. G. Heideman et al., Development of an Optical Waveguide Interferometric Immunosensor, Proceedings Eurosensor 4, Karlsruhe, 1990). The in-coupling grating and out-coupling grating may have the same or different grating periods. The (bio)chemo-functional reference layer should have no (or almost no) NSB or have the same (or almost the same) NSB as the (bio)chemo-functional signal layer. The same observations concerning sensitivity and perturbation effect as described already above are valid. In our case, however, preferably transparent substrates are applied in order to permit the incidence of light from the substrate side.

Figure 12:
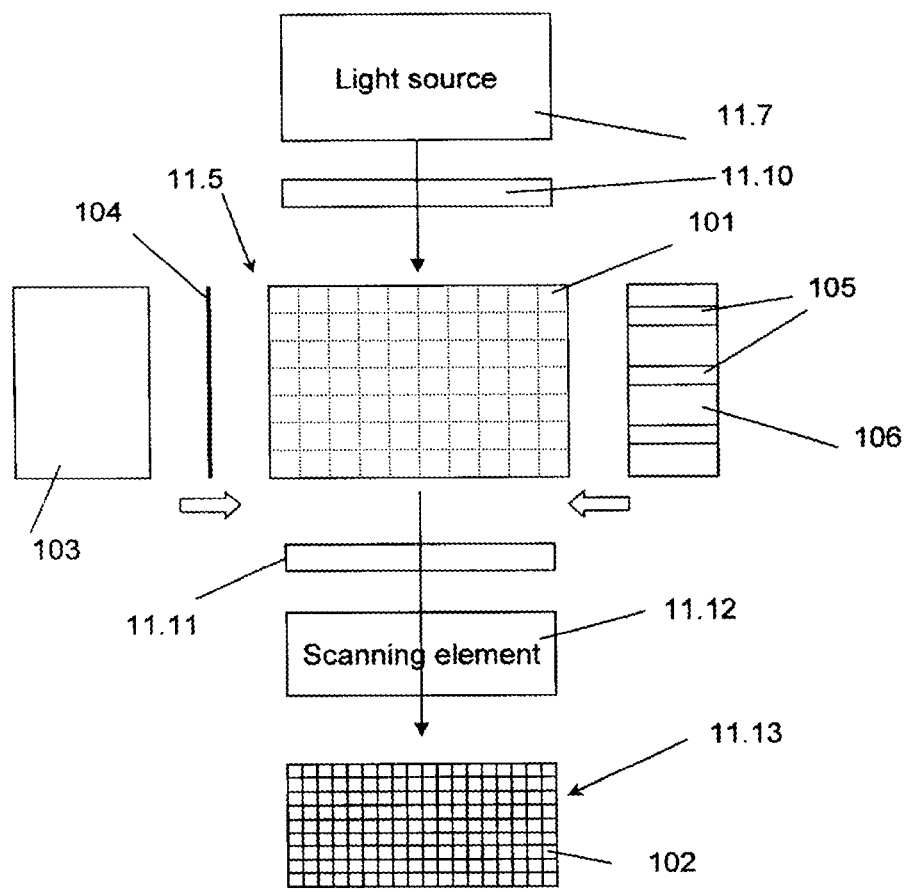
FIG. 12 shows, in a schematic manner, an optical sensor.

In FIG. 12, an embodiment of an optical sensor according to the invention is shown very schematically. The Figure illustrates the broadband light source 11.7, from which light gets, through the lens system 11.10 onto the waveguide grating structure 11.5 with a plurality of waveguide grating structure units 101. Light emitted by the waveguide grating structure and/or coupled out from the waveguide grating structure 11.5 gets via the lens system 11.11 and the scanning element 11.12 onto the detector 11.13 which includes an array of detectors 102 such as a pixel array. The waveguide grating structure is carried by a glass or plastic substrate 103, and an inorganic layer 104 may be arranged between the substrate and the waveguide grating structure 11.5. An array of liquid holders is located above the waveguide grating structure, the array of liquid holders including an array of wells 105 of a well plate 106.

What is claimed is:

1. A sensor, comprising:
    at least one light source for producing at least one incident light field;
    a sensor chip for interacting with at least one sample, the sensor chip comprising:
        a substrate;
        a one-dimensional or two-dimensional array of liquid holders or sample accommodating devices for accommodating at least one sample; and
        a waveguide grating structure on the substrate, the waveguide grating structure comprising at least one waveguide grating and having a one-dimensional or two-dimensional array of waveguide grating structure units or sensor locations, wherein at least one of the waveguide grating structure units or sensor locations comprises a signal sensing pad covered at least partially by a chemofunctional signal layer and a reference sensing pad covered at least partially by a chemofunctional reference layer, wherein the sample contacts the chemofunctional signal layer and the chemofunctional reference layer in a same one of the liquid holders or sample accommodating devices, wherein a sensitivity of an effective refractive index N with respective to a perturbation effect ΔX is the same for the signal sensing pad and the reference sensing pad, and wherein the waveguide grating structure emits at least one light field when the incident light field at least partially illuminates the waveguide grating structure;
    and at least one detector device.

2. The sensor of claim 1, further comprising at least one linker layer or modified surface between:
    (a) the chemofunctional signal layer and the waveguide grating structure;
    (b) the chemofunctional reference layer and the waveguide grating structure; or
    (c) both.

3. The sensor of claim 1, wherein the chemofunctional reference layer is free of nonspecific binding (NSB).

4. The sensor of claim 1, wherein the perturbation effect ΔX is a temperature fluctuation ΔT.

5. The sensor of claim 1, further comprising a lens system located between the waveguide grating structure and the detector device to influence the light field emitted from the waveguide grating structure, wherein the lens system operates in an imaging manner or in an almost imaging manner.

6. The sensor of claim 1, wherein the signal sensing pad or the reference sensing pad or both comprise at least two waveguide gratings with a waveguide structure region between the two waveguide gratings.

7. The sensor of claim 6, wherein the signal sensing pad is covered at least partially by the chemofunctional signal layer in the waveguide structure region between the two waveguide gratings or the reference sensing pad is covered at least partially by the chemofunctional reference layer in the waveguide structure region between the two waveguide gratings or both.

8. A sensor chip for interacting with at least one sample, the sensor chip comprising:
    a substrate;
    a one-dimensional or two-dimensional array of liquid holders or sample accommodating devices for accommodating at least one sample; and
    a waveguide grating structure on the substrate, the waveguide grating structure comprising at least one waveguide grating and having a one-dimensional or two-dimensional array of waveguide grating structure units or sensor locations,
    wherein at least one of the waveguide grating structure units or sensor locations comprises a signal sensing pad and a reference sensing pad,
    wherein the signal sensing pad or the reference sensing pad or both comprise at least two waveguide gratings with a waveguide structure region between the two waveguide gratings,
    wherein the signal sensing pad is covered at least partially by a chemofunctional signal layer,
    and wherein
        either the reference sensing pad is covered at least partially by a chemofunctional reference layer, and the sample contacts the chemofunctional signal layer and the chemofunctional reference layer in a same one of the liquid holders or sample accommodating devices,
        or a first sample contacts the chemofunctional signal layer in a first liquid holder or sample accommodating device, and a second sample, being the same or different from the first sample, or a liquid contacts at least partially the reference sensing pad in a second liquid holder or sample accommodating device,
    wherein a sensitivity of an effective refractive index N with respect to a perturbation effect ΔX is the same for the signal sensing pad and the reference sensing pad.

9. The sensor of claim 8, wherein the reference sensing pad corresponding to the second liquid holder or sample accommodating device is covered at least partially by a chemofunctional reference layer.

10. The sensor of claim 9, further comprising a linked layer or modified surface between the chemofunctional reference layer and the waveguide grating structure.

11. The sensor of claim 9, wherein the chemofunctional reference layer contacts at least partially the waveguide structure region between the two waveguide gratings.

12. The sensor of claim 8, further comprising at least one linker layer or modified surface between: (a) the chemofunctional signal layer and the waveguide grating structure; (b) the chemofunctional reference layer and the waveguide grating structure; or(c) both.

13. The sensor of claim 8, wherein the chemofunctional signal layer or the chemofunctional reference layer or both contact at least partially the waveguide structure region between the two waveguide gratings.

14. A sensor, comprising:
    at least one light source for producing at least one incident light field;

a sensor chip for interacting with at least one sample, comprising:

a substrate;

a one-dimensional or two-dimensional array of liquid holders or sample accommodating devices for accommodating at least one sample; and a waveguide grating structure on the substrate, the waveguide grating structure comprising at least one waveguide grating and having a one-dimensional or two-dimensional array of waveguide grating structure units or sensor locations, wherein at least one of the waveguide grating structure units or sensor locations comprises a signal sensing pad and a reference sensing pad and wherein the signal sensing pad is covered at least partially by a chemofunctional signal layer, wherein a first sample contacts the chemofunctional signal layer in a first liquid holder or sample accommodating device, and a second sample, being the same or different from the first sample, or a liquid contacts at least partially the reference sensing pad in a second liquid holder or sample accommodating device, wherein a sensitivity of an effective refractive index N with respect to a perturbation effect $\Delta X$ is the same for the signal sensing pad and the reference sensing pad, and wherein the waveguide grating structure emits at least one light field when the incident light field at least partially illuminates the waveguide grating structure;

and at least one detector device.

15. The sensor of claim 14, wherein the signal sensing pad or the reference sensing pad or both comprise at least two waveguide gratings with a waveguide structure region between the two waveguide gratings.

16. The sensor of claim 14, wherein the reference sensing pad is covered at least partially by a chemofunctional reference layer.

17. The sensor of claim 16, further comprising a linker layer or modified surface between the chemofunctional reference layer and the waveguide grating structure.

18. The sensor of claim 14, further comprising a linker layer or modified surface between the chemofunctional signal layer and the waveguide grating structure.

* * * * *